US009566195B2

(12) United States Patent
Lawson et al.

(10) Patent No.: US 9,566,195 B2
(45) Date of Patent: *Feb. 14, 2017

(54) ABSORBENT ARTICLE WITH WAISTBAND HAVING CONTRACTION

(71) Applicant: The Procter & Gamble Company, Cincinnati, OH (US)

(72) Inventors: Kathleen Marie Lawson, West Chester, OH (US); Jeromy Thomas Raycheck, South Lebanon, OH (US); Kathleen Ann Murphy Maciag, Cincinnati, OH (US); Raymond Scott Hamilton, Lebanon, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/146,946

(22) Filed: May 5, 2016

(65) Prior Publication Data
US 2016/0242969 A1 Aug. 25, 2016

Related U.S. Application Data

(63) Continuation of application No. 13/490,543, filed on Jun. 7, 2012, now Pat. No. 9,358,161.

(60) Provisional application No. 61/499,290, filed on Jun. 21, 2011.

(51) Int. Cl.
*A61F 13/15* (2006.01)
*A61F 13/20* (2006.01)
*A61F 13/49* (2006.01)

(52) U.S. Cl.
CPC ............... *A61F 13/49011* (2013.01); *A61F 2013/49025* (2013.01); *A61F 2013/49093* (2013.01)

(58) Field of Classification Search
CPC ............... A61F 13/49007; A61F 13/49009; A61F 13/49011; A61F 13/49012; A61F 13/49019; A61F 13/4902; A61F 2013/49007; A61F 2013/49009; A61F 2013/4902; A61F 2013/49025; A61F 2013/49026; A61F 2013/49028; A61F 2013/49036
(Continued)

(56) References Cited

U.S. PATENT DOCUMENTS

| 3,848,594 A | 11/1974 | Buell |
| 3,860,003 A | 1/1975 | Buell |
| 4,324,245 A | 4/1982 | Mesek |

(Continued)

FOREIGN PATENT DOCUMENTS

| CA | 2 311 469 A1 | 6/2000 |
| EP | 0 403 832 B1 | 1/1994 |

(Continued)

OTHER PUBLICATIONS

International Search Report, PCT/US2012/041216, mailed Aug. 6, 2012, 10 pages.

*Primary Examiner* — Michele M Kidwell
(74) *Attorney, Agent, or Firm* — Andrew J. Mueller

(57) ABSTRACT

A disposable absorbent article comprising a first waist region, a second waist region, a crotch region disposed between the first waist region and second waist region; a first waist edge and a second waist edge; the disposable absorbent article comprising a first waistband near the first waist edge and a second waistband near the second waist edge, wherein the Front-to-Back Delta Chassis Contraction is greater than about 9.0%.

20 Claims, 8 Drawing Sheets

(58) Field of Classification Search
USPC .......... 604/385.01, 385.24, 385.27, 396, 604/386–387, 385.03
See application file for complete search history.

(56) References Cited

U.S. PATENT DOCUMENTS

| | | | |
|---|---|---|---|
| 4,552,795 A | 11/1985 | Hansen et al. |
| 4,610,678 A | 9/1986 | Weisman et al. |
| 4,639,390 A | 1/1987 | Shoji et al. |
| 4,662,875 A | 5/1987 | Hirotsu et al. |
| 4,673,402 A | 6/1987 | Weisman et al. |
| 4,699,622 A | 10/1987 | Toussant et al. |
| 4,808,252 A | 2/1989 | Lash |
| 4,834,735 A | 5/1989 | Alemany et al. |
| 4,846,815 A | 7/1989 | Scripps |
| 4,883,549 A | 11/1989 | Frost et al. |
| 4,888,231 A | 12/1989 | Angstadt |
| 4,892,536 A | 1/1990 | DesMarais et al. |
| 4,894,060 A | 1/1990 | Nestegard |
| 4,909,803 A | 3/1990 | Aziz et al. |
| 4,923,660 A | 5/1990 | Willenberg et al. |
| 4,946,527 A | 8/1990 | Battrell |
| 4,963,140 A | 10/1990 | Robertson et al. |
| 4,990,147 A | 2/1991 | Freeland |
| 5,021,051 A | 6/1991 | Hiuke |
| 5,037,416 A | 8/1991 | Allen et al. |
| 5,061,261 A | 10/1991 | Suzuki et al. |
| 5,137,537 A | 8/1992 | Herron et al. |
| 5,147,345 A | 9/1992 | Young et al. |
| 5,151,092 A | 9/1992 | Buell et al. |
| 5,156,793 A | 10/1992 | Buell et al. |
| 5,167,653 A | 12/1992 | Igaue et al. |
| 5,167,897 A | 12/1992 | Weber et al. |
| 5,171,391 A | 12/1992 | Chmielewski et al. |
| 5,196,000 A | 3/1993 | Clear et al. |
| 5,221,274 A | 6/1993 | Buell et al. |
| 5,242,436 A | 9/1993 | Weil et al. |
| 5,260,345 A | 11/1993 | Desmarais et al. |
| 5,269,775 A | 12/1993 | Freeland et al. |
| 5,281,207 A | 1/1994 | Chmielewski et al. |
| 5,342,338 A | 8/1994 | Roe |
| 5,387,207 A | 2/1995 | Dyer et al. |
| 5,397,316 A | 3/1995 | Lavon et al. |
| 5,486,418 A | 1/1996 | Ohmory et al. |
| 5,499,978 A | 3/1996 | Buell et al. |
| 5,507,736 A | 4/1996 | Clear et al. |
| 5,509,905 A | 4/1996 | Michel |
| 5,545,158 A | 8/1996 | Jessup |
| 5,554,145 A | 9/1996 | Roe et al. |
| 5,569,234 A | 10/1996 | Buell et al. |
| 5,571,096 A | 11/1996 | Dobrin et al. |
| 5,575,785 A | 11/1996 | Gryskiewicz et al. |
| 5,576,090 A | 11/1996 | Suzuki |
| 5,580,411 A | 12/1996 | Nease et al. |
| 5,584,828 A | 12/1996 | Yamamoto et al. |
| 5,591,152 A | 1/1997 | Buell et al. |
| 5,607,760 A | 3/1997 | Roe |
| 5,609,587 A | 3/1997 | Roe |
| 5,625,222 A | 4/1997 | Yoneda et al. |
| 5,635,191 A | 6/1997 | Roe et al. |
| 5,643,243 A | 7/1997 | Klemp |
| 5,643,588 A | 7/1997 | Roe et al. |
| 5,672,166 A | 9/1997 | Vandemoortele |
| 5,674,215 A | 10/1997 | Ronnberg |
| 5,681,302 A | 10/1997 | Melbye et al. |
| 5,749,865 A | 5/1998 | Yamamoto et al. |
| 5,827,259 A | 10/1998 | Laux et al. |
| 5,827,387 A | 10/1998 | Reynolds et al. |
| 5,865,823 A | 2/1999 | Curro |
| 5,879,341 A | 3/1999 | Odorzynski et al. |
| 5,895,382 A | 4/1999 | Popp et al. |
| 5,904,675 A | 5/1999 | Laux et al. |
| 5,911,713 A | 6/1999 | Yamada et al. |
| 5,931,825 A | 8/1999 | Kuen et al. |
| 5,931,826 A | 8/1999 | Faulks et al. |
| 5,942,179 A | 8/1999 | Tallentire et al. |
| 5,993,433 A | 11/1999 | St. Louis et al. |
| 6,004,306 A | 12/1999 | Robles et al. |
| 6,107,537 A | 8/2000 | Elder et al. |
| 6,117,121 A | 9/2000 | Faulks et al. |
| 6,120,486 A | 9/2000 | Toyoda et al. |
| 6,120,487 A | 9/2000 | Ashton |
| 6,123,694 A | 9/2000 | Pieniak et al. |
| 6,171,290 B1 | 1/2001 | Boisse et al. |
| 6,174,302 B1 | 1/2001 | Kumasaka |
| 6,186,996 B1 | 2/2001 | Martin |
| 6,248,097 B1 | 6/2001 | Beitz et al. |
| 6,264,642 B1 | 7/2001 | Kuen et al. |
| 6,264,643 B1 | 7/2001 | Toyoda |
| 6,293,934 B1 | 9/2001 | Kumasaka |
| 6,346,162 B1 | 2/2002 | Reynolds et al. |
| 6,375,646 B1 | 4/2002 | Widlund et al. |
| 6,413,249 B1 | 7/2002 | Turi et al. |
| 6,432,098 B1 | 8/2002 | Kline et al. |
| 6,436,216 B1 | 8/2002 | Grover |
| 6,440,117 B1 | 8/2002 | Itoh et al. |
| 6,451,001 B2 | 9/2002 | Kumasaka |
| 6,461,342 B2 | 10/2002 | Tanji et al. |
| 6,478,785 B1 | 11/2002 | Ashton et al. |
| 6,494,872 B1 | 12/2002 | Suzuki et al. |
| 6,527,893 B1 | 3/2003 | Boisse et al. |
| 6,552,123 B1 | 4/2003 | Katayama et al. |
| 6,569,139 B1 | 5/2003 | Datta et al. |
| 6,569,140 B1 | 5/2003 | Mizutani et al. |
| 6,592,562 B2 | 7/2003 | Menard et al. |
| 6,595,976 B2 | 7/2003 | Jitoe et al. |
| 6,605,752 B2 | 8/2003 | Magnusson et al. |
| 6,613,033 B1 | 9/2003 | Popp et al. |
| 6,629,967 B1 | 10/2003 | Simmons et al. |
| 6,638,262 B2 | 10/2003 | Suzuki et al. |
| 6,641,692 B2 | 11/2003 | Reynolds et al. |
| 6,659,990 B1 | 12/2003 | Odorzynski et al. |
| 6,682,515 B1 | 1/2004 | Mizutani et al. |
| 6,682,516 B2 | 1/2004 | Johnston et al. |
| 6,699,228 B1 | 3/2004 | Chmielewski et al. |
| 6,706,029 B1 | 3/2004 | Suzuki et al. |
| 6,706,030 B1 | 3/2004 | Okuda et al. |
| 6,767,343 B2 | 7/2004 | Shimada et al. |
| 6,808,582 B2 | 10/2004 | Popp et al. |
| 6,837,958 B2 | 1/2005 | Otsubo et al. |
| 6,884,310 B2 | 4/2005 | Roessler et al. |
| 6,902,793 B2 | 6/2005 | Ukegawa et al. |
| 6,978,486 B2 | 12/2005 | Zhou et al. |
| 7,037,300 B2 | 5/2006 | Kling |
| 7,150,729 B2 | 12/2006 | Shimada et al. |
| 7,163,530 B1 | 1/2007 | Toyoshima et al. |
| 7,169,136 B2 | 1/2007 | Otsubo et al. |
| 7,189,219 B1 | 3/2007 | Kasai et al. |
| 7,195,621 B2 | 3/2007 | Ohnishi et al. |
| 7,207,978 B2 | 4/2007 | Takino et al. |
| 7,226,437 B2 | 6/2007 | Sasaki et al. |
| 7,264,686 B2 | 9/2007 | Thorson et al. |
| 7,291,138 B2 | 11/2007 | Hoshino et al. |
| 7,331,946 B2 | 2/2008 | Shimada et al. |
| 7,338,479 B2 | 3/2008 | Rujioka et al. |
| 7,378,360 B2 | 5/2008 | Clark et al. |
| 7,435,243 B2 | 10/2008 | Miyamoto |
| 7,435,244 B2 | 10/2008 | Schroer et al. |
| 7,527,616 B2 | 5/2009 | Miyamoto |
| 7,561,602 B1 | 7/2009 | Nakabayashi |
| 7,569,039 B2 | 8/2009 | Matsuda et al. |
| 7,604,625 B2 | 10/2009 | Turi et al. |
| 7,621,900 B2 | 11/2009 | Van Gmpel et al. |
| 7,666,176 B2 | 2/2010 | Erdman et al. |
| 7,670,325 B2 | 3/2010 | Sugiyama et al. |
| 7,708,725 B2 | 5/2010 | Kinoshita et al. |
| 7,727,214 B2 | 6/2010 | Torigoshi et al. |
| 7,744,576 B2 | 6/2010 | Busam et al. |
| 7,744,579 B2 | 6/2010 | Langdon et al. |
| 7,750,203 B2 | 7/2010 | Becker et al. |
| 7,753,899 B2 | 7/2010 | Mori et al. |
| 7,754,040 B2 | 7/2010 | Norrby |
| 7,785,309 B2 | 8/2010 | Van Gompel et al. |
| 7,794,441 B2 | 9/2010 | Ashton et al. |

(56) References Cited

U.S. PATENT DOCUMENTS

| | | |
|---|---|---|
| 7,834,236 B2 | 11/2010 | Middlesworth et al. |
| 7,918,839 B2 | 4/2011 | Ehrnsperger et al. |
| 7,918,840 B2 | 4/2011 | Corneliusson |
| 8,002,760 B2 | 8/2011 | Ehrnsperger et al. |
| 8,038,662 B2 | 10/2011 | Hornung et al. |
| 8,043,274 B2 | 10/2011 | Mlinar et al. |
| 8,043,275 B2 | 10/2011 | Peterson |
| 8,062,279 B2 | 11/2011 | Miyamoto |
| 8,075,543 B2 | 12/2011 | Okuda |
| 8,105,303 B2 | 1/2012 | Sakaguchi |
| 8,114,059 B2 | 2/2012 | Ehrnsperger et al. |
| 8,182,627 B2 | 5/2012 | Eckstein et al. |
| 8,212,102 B2 | 7/2012 | Kumasaka |
| 8,328,782 B2 | 12/2012 | Catalan et al. |
| 8,333,749 B2 | 12/2012 | Tsang et al. |
| 8,348,919 B2 | 1/2013 | Langdon et al. |
| 8,377,023 B2 | 2/2013 | Sawyer et al. |
| 8,475,424 B2 | 7/2013 | Fujimoto et al. |
| 8,496,638 B2 | 7/2013 | Lord et al. |
| 8,513,483 B2 | 8/2013 | Tee et al. |
| 8,518,010 B2 | 8/2013 | Kuwano et al. |
| 8,551,064 B2 | 10/2013 | Lavon et al. |
| 8,568,566 B2 | 10/2013 | Jackels et al. |
| 8,663,184 B2 | 3/2014 | Liu et al. |
| 8,679,084 B2 | 3/2014 | Kurihara |
| 8,777,918 B2 | 7/2014 | Kuwano et al. |
| 8,795,250 B2 | 8/2014 | O'Connell |
| 8,939,957 B2 | 1/2015 | Raycheck et al. |
| 9,066,838 B2 | 6/2015 | Hippe et al. |
| 9,089,455 B2 | 7/2015 | Raycheck et al. |
| 9,358,161 B2* | 6/2016 | Lawson ............ A61F 13/49011 |
| 2002/0128626 A1 | 9/2002 | Friderich et al. |
| 2002/0177829 A1 | 11/2002 | Fell et al. |
| 2003/0023220 A1 | 1/2003 | Ukegawa et al. |
| 2004/0002690 A1 | 1/2004 | Miyamoto |
| 2004/0122400 A1* | 6/2004 | Hancock-Cooke . A61F 13/4902 604/385.3 |
| 2004/0127876 A1 | 7/2004 | Stevens |
| 2004/0129597 A1 | 7/2004 | Guzmann et al. |
| 2004/0158217 A1 | 8/2004 | Wu et al. |
| 2004/0222553 A1 | 11/2004 | Desai et al. |
| 2004/0243085 A1 | 12/2004 | Veith et al. |
| 2005/0003048 A1 | 1/2005 | Pearce et al. |
| 2005/0004549 A1 | 1/2005 | Maas et al. |
| 2005/0095700 A1 | 5/2005 | Budzowski et al. |
| 2005/0106971 A1* | 5/2005 | Thomas ............. A41D 31/0016 442/181 |
| 2005/0113790 A1 | 5/2005 | Suzuki |
| 2005/0177123 A1 | 8/2005 | Catalan |
| 2005/0203479 A1 | 9/2005 | Sakaguchi et al. |
| 2005/0215155 A1 | 9/2005 | Young et al. |
| 2005/0281757 A1 | 12/2005 | Ibrahim et al. |
| 2005/0288645 A1 | 12/2005 | LaVon |
| 2006/0014460 A1 | 1/2006 | Isele et al. |
| 2006/0111686 A1 | 5/2006 | Schneider |
| 2006/0264860 A1 | 11/2006 | Beck et al. |
| 2006/0270302 A1 | 11/2006 | Ando et al. |
| 2007/0005040 A1 | 1/2007 | Langdon et al. |
| 2007/0073259 A1 | 3/2007 | Erdman et al. |
| 2007/0088116 A1 | 4/2007 | Abba et al. |
| 2007/0123834 A1 | 5/2007 | McDowall et al. |
| 2007/0191808 A1 | 8/2007 | Toyoshima et al. |
| 2007/0287983 A1 | 12/2007 | Lodge et al. |
| 2008/0077111 A1 | 3/2008 | Erdman et al. |
| 2008/0195070 A1 | 8/2008 | Ponomarenko et al. |
| 2008/0195071 A1 | 8/2008 | Ponomarenko et al. |
| 2008/0312617 A1 | 12/2008 | Hundorf et al. |
| 2008/0312631 A1 | 12/2008 | Okuda |
| 2009/0157034 A1 | 6/2009 | Mattingly et al. |
| 2009/0159187 A1 | 6/2009 | Ashraf |
| 2009/0182298 A1 | 7/2009 | Kumasaka |
| 2009/0312734 A1 | 12/2009 | Lavon et al. |
| 2010/0028638 A1 | 2/2010 | Reichardt et al. |
| 2010/0193110 A1 | 8/2010 | Eckstein et al. |
| 2010/0305532 A1 | 12/2010 | Ashton et al. |
| 2010/0312214 A1 | 12/2010 | Shimada et al. |
| 2010/0318054 A1 | 12/2010 | Langdon et al. |
| 2011/0004177 A1 | 1/2011 | Roe et al. |
| 2011/0022019 A1 | 1/2011 | Shimada et al. |
| 2011/0066128 A1 | 3/2011 | Takahashi |
| 2011/0092944 A1 | 4/2011 | Sagasaka et al. |
| 2011/0130737 A1 | 6/2011 | Sagisaka et al. |
| 2011/0172626 A1 | 7/2011 | Mitsuno et al. |
| 2011/0178489 A1 | 7/2011 | Baba et al. |
| 2011/0196327 A1 | 8/2011 | Chhabra et al. |
| 2011/0223381 A1 | 9/2011 | Sauter et al. |
| 2011/0245792 A1 | 10/2011 | O'Connell |
| 2011/0250256 A1 | 10/2011 | Hyun-Oh et al. |
| 2012/0073760 A1 | 3/2012 | Hamada et al. |
| 2012/0277702 A1 | 11/2012 | Raycheck et al. |
| 2012/0277713 A1 | 11/2012 | Raycheck et al. |
| 2012/0289921 A1 | 11/2012 | Hashino et al. |
| 2012/0316046 A1 | 12/2012 | Jackels et al. |
| 2012/0316523 A1 | 12/2012 | Hippe et al. |
| 2012/0316526 A1 | 12/2012 | Jackels et al. |
| 2012/0316527 A1 | 12/2012 | Rosati et al. |
| 2012/0316528 A1 | 12/2012 | Kreuzer et al. |
| 2012/0316529 A1 | 12/2012 | Kreuzer et al. |
| 2012/0330262 A1 | 12/2012 | Lawson et al. |
| 2012/0330263 A1 | 12/2012 | Lawson et al. |
| 2012/0330264 A1 | 12/2012 | Lawson et al. |
| 2013/0041340 A1 | 2/2013 | Kawakami et al. |

FOREIGN PATENT DOCUMENTS

| | | |
|---|---|---|
| JP | H 10-277091 A | 10/1998 |
| JP | 2000-342623 | 12/2000 |
| JP | 2002-102279 A | 4/2002 |
| JP | 2002-209938 A | 7/2002 |
| JP | 2002-253604 A | 9/2002 |
| JP | 3488506 B2 | 1/2004 |
| JP | 3606297 | 1/2005 |
| JP | 2006-320709 A | 11/2006 |
| JP | 2009-056142 A | 3/2009 |
| JP | 4330281 B2 | 9/2009 |
| JP | 5001756 B2 | 8/2012 |
| WO | WO 94-04656 A2 | 3/1994 |
| WO | WO 95/16746 | 6/1995 |
| WO | WO 97-20532 A1 | 6/1997 |
| WO | WO 02-36059 A1 | 5/2002 |
| WO | WO 2005/095700 | 10/2005 |
| WO | WO 2006-135357 A1 | 12/2006 |

* cited by examiner

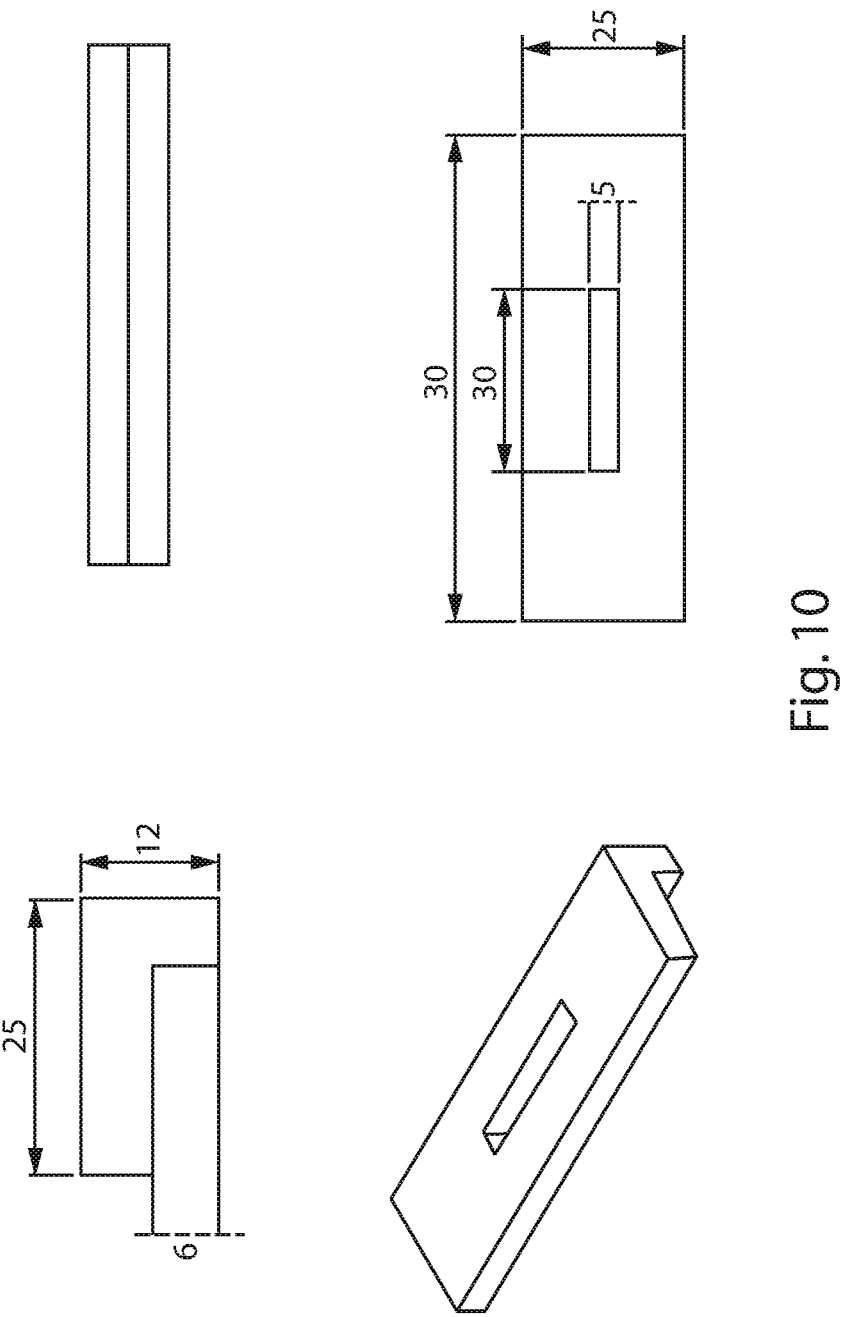

ABSORBENT ARTICLE WITH WAISTBAND HAVING CONTRACTION

CROSS REFERENCE TO RELATED APPLICATION

This application is a continuation of U.S. Nonprovisional application Ser. No. 13/490,543, filed Jun. 7, 2012, which claims the benefit of U.S. Provisional Application No. 61/499,290, filed Jun. 21, 2011, which is herein incorporated by reference in its entirety.

FIELD OF INVENTION

This invention relates to absorbent articles such as diapers having improved waistband properties that yield a more garment-like article. The absorbent article may have improved functional characteristics and communicative properties.

BACKGROUND OF THE INVENTION

Many diapers on the market today have waistbands or waist stretch elements in which a laminate of nonwovens and elastics strands are combined with the chassis under some tension. Elastic strands are the most cost effective way to get stretch that exhibits little relax or set over time. Nonwovens are preferred for the exterior of the waist material because it is breathable and softer than film alternatives. Some executions of applied waistband consist of elastics stretched in the process and applied transversely to the length of the product sandwiched in between some body-facing and some garment-facing material.

Other executions create a laminate of elastic strands and nonwoven and apply the laminate to the chassis under contraction transversely to the length of the product on the body-facing side such that the only material between the elastics and the body surface is a nonwoven in the waistband region. It is known that contraction around the waist will improve the perceived fit of the product by closing gaps at the back of the diaper, therefore, closing of these gaps could positively impact real or perceived leakage/containment. It is also known that when strands of elastic are combined under strain with other often non-extensible materials and then allowed to relax, they will create a laminate that has gathers of a certain frequency and a resulting basis weight that is higher than the starting materials laid flat. Since waistbands or stretch elements around the waist are added at full strain, when pulled tight during application, the waistbands fully extend or flatten around the waist area resulting in a basis weight around the waist similar to the starting materials. Therefore, a need exists to improve waist and leg band construction and application to the chassis to improve fit and leakage containment.

SUMMARY OF THE INVENTION

The present invention relates to a disposable absorbent article comprising: a first waist region, a second waist region, a crotch region disposed between the first waist region and second waist region; a first waist edge and a second waist edge; a first longitudinal edge and a second longitudinal edge, the disposable absorbent article comprising at least one waistband.

In one embodiment, the waistband is comprised of a laminate comprising a nonwoven material and at least one elastic strand, wherein the nonwoven material and the elastic strand are combined under a first strain and the waistband is attached to the disposable absorbent article under an applied waistband strain, such that the waistband has a Full Waistband Consolidation of greater than about 95% and/or an Extended Waistband Consolidation of greater than about 35%.

In one embodiment, the disposable absorbent article comprises a first waistband near the first waist edge and a second waistband near the second waist edge, wherein the Front-to-Back Delta Chassis Contraction is greater than about 9.0%.

In one embodiment, the disposable absorbent article comprises a leg gasketing system, wherein the waistband has a first gather count and the leg gasketing system has a second gather count such that the ratio of the first gather count to the second gather count is from about 0.75 to about 1.25.

BRIEF DESCRIPTION OF THE DRAWINGS

FIG. 10 is a schematic representation of a template.

DETAILED DESCRIPTION OF THE INVENTION

Figure 1:
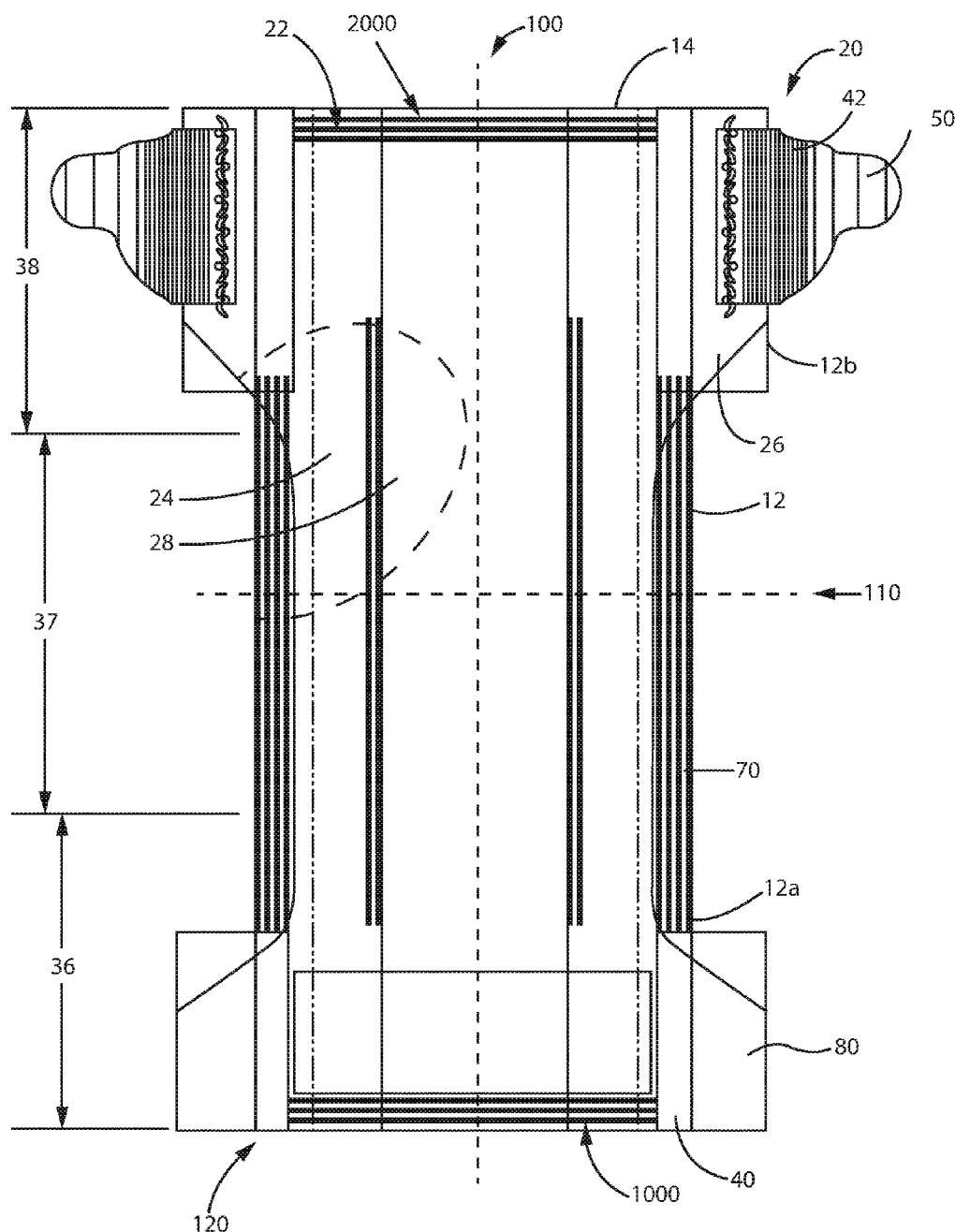
FIG. 1 is a plan view of an exemplary absorbent article.

As used herein, the following terms shall have the meaning specified thereafter:

"Disposable," in reference to absorbent articles, means that the absorbent articles are generally not intended to be laundered or otherwise restored or reused as absorbent articles (i.e., they are intended to be discarded after a single use and, preferably, to be recycled, composted or otherwise discarded in an environmentally compatible manner).

"Absorbent article" refers to devices which absorb and contain body exudates and, more specifically, refers to devices which are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like.

"Proximal" and "Distal" refer respectively to the location of an element relatively near to or far from the longitudinal or lateral centerline of a structure (e.g., the proximal edge of a longitudinally extending element is located nearer to the longitudinal centerline than the distal edge of the same element is located relative to the same longitudinal centerline).

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Longitudinal" refers to a direction running substantially perpendicular from a waist edge to an opposing waist edge of the article and generally parallel to the maximum linear dimension of the article. Directions within 45 degrees of the longitudinal direction are considered to be "longitudinal"

"Lateral" refers to a direction running from a longitudinal edge to an opposing longitudinal edge of the article and generally at a right angle to the longitudinal direction. Directions within 45 degrees of the lateral direction are considered to be "lateral."

"Disposed" refers to an element being located in a particular place or position.

"Joined" refers to configurations whereby an element is directly secured to another element by affixing the element directly to the other element and to configurations whereby an element is indirectly secured to another element by affixing the element to intermediate member(s) which in turn are affixed to the other element.

"Film" refers to a sheet-like material wherein the length and width of the material far exceed the thickness of the material. Typically, films have a thickness of about 0.5 mm or less.

"Water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water, urine, or synthetic urine to pass through its thickness in the absence of a forcing pressure. Conversely, the term "water-impermeable" refers to a layer or a layered structure through the thickness of which liquid water, urine, or synthetic urine cannot pass in the absence of a forcing pressure (aside from natural forces such as gravity). A layer or a layered structure that is water-impermeable according to this definition may be permeable to water vapor, i.e., may be "vapor-permeable."

"Extendibility" and "extensible" mean that the width or length of the component in a relaxed state can be extended or increased.

"Elasticated" and "elasticized" mean that a component comprises at least a portion made of elastic material.

"Elongatable material," "extensible material," or "stretchable material" are used interchangeably and refer to a material that, upon application of a biasing force, can stretch to an elongated length of at least about 110% of its relaxed, original length (i.e. can stretch to 10 percent more than its original length), without rupture or breakage, and upon release of the applied force, shows little recovery, less than about 20% of its elongation without complete rupture or breakage as measured by EDANA method 20.2-89. In the event such an elongatable material recovers at least 40% of its elongation upon release of the applied force, the elongatable material will be considered to be "elastic" or "elastomeric." For example, an elastic material that has an initial length of 100 mm can extend at least to 150 mm, and upon removal of the force retracts to a length of at least 130 mm (i.e., exhibiting a 40% recovery). In the event the material recovers less than 40% of its elongation upon release of the applied force, the elongatable material will be considered to be "substantially non-elastic" or "substantially non-elastomeric". For example, an elongatable material that has an initial length of 100 mm can extend at least to 150 mm, and upon removal of the force retracts to a length of at least 145 mm (i.e., exhibiting a 10% recovery).

"Elastomeric material" is a material exhibiting elastic properties. Elastomeric materials may include elastomeric films, scrims, nonwovens, and other sheet-like structures.

"Pant" refers to disposable absorbent articles having a pre-formed waist and leg openings. A pant may be donned by inserting a wearer's legs into the leg openings and sliding the pant into position about the wearer's lower torso. Pants are also commonly referred to as "closed diapers", "prefastened diapers", "pull-on diapers", "training pants" and "diaper-pants."

FIG. 1 is a plan view of an exemplary, non-limiting embodiment of an absorbent article 20 of the present invention in a flat, uncontracted state (i.e., without elastic induced contraction). The garment-facing surface 120 of the absorbent article 20 is facing the viewer. The absorbent article 20 includes a longitudinal centerline 100 and a lateral centerline 110. The absorbent article 20 may comprise a chassis 22. The absorbent article 20 and chassis 22 are shown to have a first waist region 36, a second waist region 38 opposed to the first waist region 36, and a crotch region 37 located between the first waist region 36 and the second waist region 38. The waist regions 36 and 38 generally comprise those portions of the absorbent article 20 which, when worn, encircle the waist of the wearer. The waist regions 36 and 38 may include elastic elements such that they gather about the waist of the wearer to provide improved fit and containment. The waist regions 36 and 38 may include a first waistband 1000 and a second waistband 2000. The crotch region 37 is that portion of the absorbent article 20 which, when the absorbent article 20 is worn, is generally positioned between the legs of the wearer.

The outer periphery of chassis 22 is defined by longitudinal edges 12 and lateral edges 14. The longitudinal edges 12 may be subdivided into a front longitudinal edge 12a, which is the portion of the longitudinal edge 12 in the first waist region 36, and a rear longitudinal edge 12b, which is the portion of the longitudinal edge 12 in the rear waist region 38. The chassis 22 may have opposing longitudinal edges 12 that are oriented generally parallel to the longitudinal centerline 100. However, for better fit, longitudinal edges 12 may be curved or angled to produce, for example, an "hourglass" shape diaper when viewed in a plan view. The chassis 22 may have opposing lateral edges 14 that are oriented generally parallel to the lateral centerline 110.

The chassis 22 may comprise a liquid permeable topsheet 24, a backsheet 26, and an absorbent core 28 between the topsheet 24 and the backsheet 26. The absorbent core 28 may have a body-facing surface and a garment facing-surface. The topsheet 24 may be joined to the core 28 and/or the backsheet 26. The backsheet 26 may be joined to the core 28 and/or the topsheet 24. It should be recognized that other structures, elements, or substrates may be positioned between the core 28 and the topsheet 24 and/or backsheet 26. In certain embodiments, the chassis 22 comprises the main structure of the absorbent article 20 with other features may added to form the composite diaper structure. While the topsheet 24, the backsheet 26, and the absorbent core 28 may be assembled in a variety of well-known configurations, preferred diaper configurations are described generally in U.S. Pat. Nos. 3,860,003; 5,151,092; 5,221,274; 5,554,145; 5,569,234; 5,580,411; and 6,004,306.

The topsheet 24 is generally a portion of the absorbent article 20 that may be positioned at least in partial contact or close proximity to a wearer. Suitable topsheets 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. The topsheet 24 is generally supple, soft feeling, and non-irritating to a wearer's skin. Generally, at least a portion of the topsheet 24 is liquid pervious, permitting liquid to readily penetrate through the thickness of the topsheet 24. The topsheet 24 may include apertures. One topsheet 24 useful herein is available from BBA Fiberweb, Brentwood, Tenn. as supplier code 055SLPV09U.

Any portion of the topsheet 24 may be coated with a lotion or skin care composition as is known in the art. Examples of suitable lotions include those described in U.S. Pat. Nos. 5,607,760; 5,609,587; 5,635,191; and 5,643,588. The topsheet 24 may be fully or partially elasticized or may be foreshortened so as to provide a void space between the topsheet 24 and the core 28. Exemplary structures including elasticized or foreshortened topsheets are described in more detail in U.S. Pat. Nos. 4,892,536; 4,990,147; 5,037,416; and 5,269,775.

The absorbent core 28 may comprise a wide variety of liquid-absorbent materials commonly used in disposable diapers and other absorbent articles. Examples of suitable absorbent materials include comminuted wood pulp, which is generally referred to as air felt creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. In one embodiment, at least a portion of the absorbent core is substantially cellulose free and contains less than 10% by weight cellulosic fibers, less than 5% cellulosic fibers, less than 1% cellulosic fibers, no more than an immaterial amount of cellulosic fibers or no cellulosic fibers. It should be understood that an immaterial amount of cellulosic material does not materially affect at least one of the thinness, flexibility, and absorbency of the portion of the absorbent core that is substantially cellulose free. Among other benefits, it is believed that when at least a portion of the absorbent core is substantially cellulose free, this portion of the absorbent core is significantly thinner and more flexible than a similar absorbent core that includes more than 10% by weight of cellulosic fibers. The amount of absorbent material, such as absorbent particulate polymer material present in the absorbent core may vary, but in certain embodiments, is present in the absorbent core in an amount greater than about 80% by weight of the absorbent core, or greater than about 85% by weight of the absorbent core, or greater than about 90% by weight of the absorbent core, or greater than about 95% by weight of the core. Non-limiting examples of suitable absorbent cores are described in greater details below.

Exemplary absorbent structures for use as the absorbent core 28 are described in U.S. Pat. Nos. 4,610,678; 4,673, 402; 4,834,735; 4,888,231; 5,137,537; 5,147,345; 5,342, 338; 5,260,345; 5,387,207; 5,397,316; and 5,625,222.

The backsheet 26 is generally positioned such that it may be at least a portion of the garment-facing surface 120 of the absorbent article 20. Backsheet 26 may be designed to prevent the exudates absorbed by and contained within the absorbent article 20 from soiling articles that may contact the absorbent article 20, such as bed sheets and undergarments. In certain embodiments, the backsheet 26 is substantially water-impermeable. Suitable backsheet 26 materials include films such as those manufactured by Tredegar Industries Inc. of Terre Haute, Ind. and sold under the trade names X15306, X10962, and X10964. Other suitable backsheet 26 materials may include breathable materials that permit vapors to escape from the absorbent article 20 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746 and U.S. Pat. No. 5,865,823. Other breathable backsheets including nonwoven webs and apertured formed films are described in U.S. Pat. No. 5,571,096. An exemplary, suitable backsheet is disclosed in U.S. Pat. No. 6,107,537. Other suitable materials and/or manufacturing techniques may be used to provide a suitable backsheet 26 including, but not limited to, surface treatments, particular film selections and processing, particular filament selections and processing, etc.

Backsheet 26 may also consist of more than one layer. The backsheet 26 may comprise an outer cover and an inner layer. The outer cover may be made of a soft, non-woven material. The inner layer may be made of a substantially liquid-impermeable film. The outer cover and an inner layer may be joined together by adhesive or any other suitable material or method. A particularly suitable outer cover is available from Corovin GmbH, Peine, Germany as supplier code A18AH0, and a particularly suitable inner layer is available from RKW Gronau GmbH, Gronau, Germany as supplier code PGBR4WPR. While a variety of backsheet configurations are contemplated herein, it would be obvious to those skilled in the art that various other changes and modifications can be made without departing from the spirit and scope of the invention.

The absorbent article 20 may include front ears 40 and/or back ears 42. The ears 40, 42 may be extensible, inextensible, elastic, or inelastic. The ears 40, 42 may be formed from nonwoven webs, woven webs, knitted fabrics, polymeric and elastomeric films, apertured films, sponges, foams, scrims, and combinations and laminates thereof. In certain embodiments the ears 40, 42 may be formed of a stretch laminate such as a nonwoven/elastomeric material laminate or a nonwoven/elastomeric material/nonwoven laminate. Stretch laminates may be formed by any method known in the art. For example, the ears 40, 42 may be formed as a zero strain stretch laminate, which includes at least a layer of non-woven material and an elastomeric element. The elastomeric element is attached to the layer of non-woven material while in a relaxed or substantially relaxed state, and the resulting laminate is made stretchable (or more stretchable over a further range) by subjecting the laminate to an activation process which elongates the nonwoven layer permanently, but the elastomeric element temporarily. The nonwoven layer may be integral with at least a portion of the chassis 22, in which case the elastomeric element may be attached to the nonwoven layer and the non-woven/elastomeric element laminate is subsequently activated. Alternatively, the nonwoven layer may be a separate component, in which case the elastomeric element is attached to the nonwoven layer to form the laminate, which is then coupled to the main portion. If one or more layers of the side panel are provided separately, the laminate may be activated either before or after attachment to the main portion. The zero strain activation processes is further disclosed in U.S. Pat. Nos. 5,167,897 and 5,156,793. A suitable elastic ear may be an activated laminate comprising an elastomeric film (such as is available from Tredegar Corp, Richmond, Va., as supplier code X25007) disposed between two nonwoven layers (such as is available from BBA Fiberweb, Brentwood, Tenn. as supplier code FPN332).

The ears 40, 42 may be discrete or integral. A discrete ear is formed as separate element which is joined to the chassis 22. An integral ear is a portion of the chassis 22 that projects laterally outward from the longitudinal edge 12. The integral ear may be formed by cutting the chassis form to include the shape of the ear projection.

The absorbent article 20 may also include a fastening system 50. When fastened, the fastening system 50 interconnects the first waist region 36 and the second waist region 38 resulting in a waist circumference that may encircle the wearer during wear of the absorbent article 20. The fastening system 50 may comprises a fastener such as tape tabs, hook and loop fastening components, interlocking fasteners such as tabs & slots, buckles, buttons, snaps, and/or hermaphroditic fastening components, although any other known fastening means are generally acceptable. Some exemplary surface fastening systems are disclosed in U.S. Pat. Nos. 3,848,594; 4,662,875; 4,846,815; 4,894,060; 4,946,527; 5,151,092; and 5,221,274. An exemplary interlocking fastening system is disclosed in U.S. Pat. No. 6,432,098. The fastening system 50 may also provide a means for holding the article in a disposal configuration as disclosed in U.S. Pat. No. 4,963,140. The fastening system 50 may also include primary and secondary fastening systems, as disclosed in U.S. Pat. No. 4,699,622. The fastening system 50 may be constructed to reduce shifting of overlapped portions or to improve fit as disclosed in U.S. Pat. Nos. 5,242,436; 5,499,978; 5,507,736; and 5,591,152.

Waistbands of the present invention may result in absorbent articles having increased comfort, fit, and improved leakage performance for the wearer. Certain waistbands may also provide improved product durability and strength. The waistbands of the present invention may also result an easier and improved absorbent article changing experience.

One object of the present invention is to deliver an absorbent article having improved gap closure in the first and/or second waist regions of the absorbent article than what is currently known in the art today. Having gap closure in the waist regions may create an article with better fit and containment, resulting in improved leakage performance. One way to achieve gap closure is to provide a waistband that is flush coterminous with the rear lateral edge of the absorbent article. Because there is variation in the application process, in some embodiments, a waistband may be present in both the first and second waist regions of the absorbent article. However, while a highly contracted waistband is desirable for the back waist region to provide stretch, it may be more desirable to have a less contracted waistband in the front waist region to aid in application. Therefore, one embodiment of the present invention is directed to "differential contraction" or waistband laminates having different installed elongation strands in the front versus the back, such that only one waistband laminate is cut. Cutting of the waistband laminate is subsequent to the waistband application to the article; the waistband is applied such that it spans the intended article separation (cut) zone. Thus, the same waistband laminate can deliver different levels of contraction in the back and front, resulting in higher contraction in the back to help close the gap and lower contraction in the front.

In one embodiment, the first (1000) and second waistbands (2000) are comprised of a waistband laminate (3000). In one embodiment, the waistband laminate is comprised of a nonwoven material (3100). In one embodiment, the waistband laminate is comprised of a film. In one embodiment, the waistband laminate is comprised of at least two elastic strands (3200), at least four elastic strands, at least six elastic strands, at least eight elastic strands, at least ten elastic strands, at least twelve elastic strands. In one embodiment, the first and second waistbands are applied to the article at the same applied waistband strain. In one embodiment, the first waistband and the second waistband are applied to the disposable absorbent article at a strain of greater than about 30%, greater than about 50%, greater than about 70% as compared to the relaxed length. In one embodiment, the first waistband and the second waistband are applied to the disposable absorbent article at a strain of less than about 150%, less than about 125%, less than about 100%, less than about 75% as compared to the relaxed length. In one embodiment, the first waistband and the second waistband are applied to the disposable absorbent article at a strain of from about 70% to about 75% as compared to the relaxed length.

In one embodiment, the waistband laminate is comprised of a nonwoven material and at least two elastic strands, wherein each of the at least two elastic strands are different elastic materials. In one embodiment, the elastic strands have different diameters or cross-sectional geometry.

Figure 2:
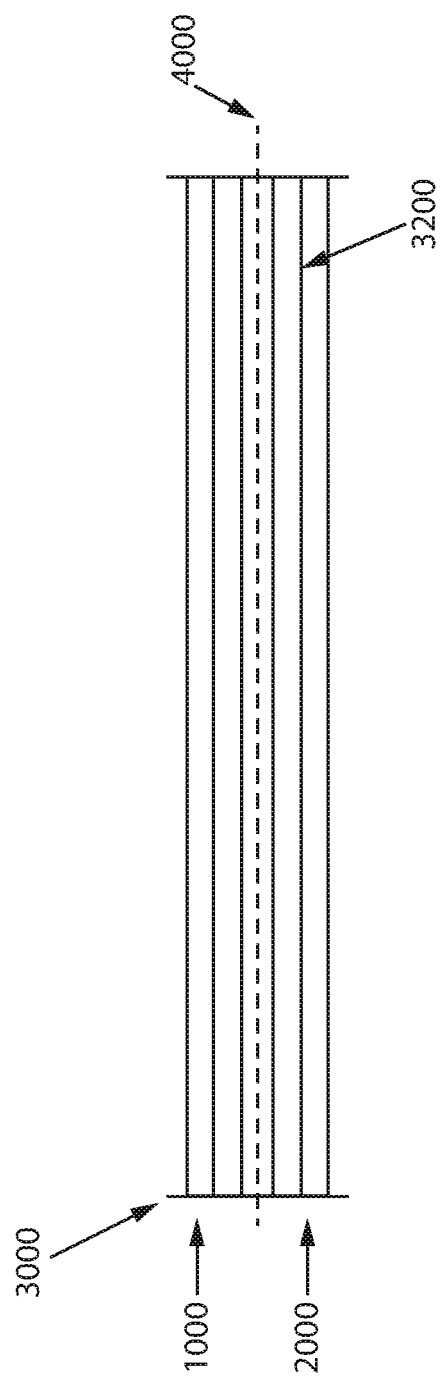
FIG. 2 is a plan view of a waistband laminate suitable in one embodiment of the invention.

In one embodiment, the waistband laminate is cut after application to the article between the elastic strands such that a waistband laminate comprised of at least two elastic strands results in two waistbands each having one elastic strand; a waistband laminate comprised of at least four elastic strands results in two waistbands each having two elastic strands. As shown in FIG. 2, a waistband laminate 3000 comprised of at least six elastic strands results in two waistbands (1000, 2000) each having three elastic strands when cut (cut line 4000). Further, a waistband laminate comprised of at least eight elastic strands results in two waistbands each having four elastic strands, a waistband laminate comprised of at least ten elastic strands results in two waistbands each having five elastic strands, a waistband laminate comprised of at least twelve elastic strands results in two waistbands each having six elastic strands. In one embodiment, the waistband laminate is cut such that the two resulting waistbands have an unequal distribution of elastic strands or having no elastic strands on one side of the cut. For example, a waistband laminate having ten elastic strands may result in one waistband having six elastics and one waistband having four elastics. In another example, a waistband laminate having ten elastic strands may result in one waistband having ten elastics and one waistband having no elastics. In one embodiment, the waistband laminate is cut in the center to create the two waistbands. In one embodiment, the waistband laminate is cut off-center. In one embodiment, the waistband laminate may have elastic strands spaced equally apart. In one embodiment, the waistband laminate may have strands spaced closer together or further apart as compared to the other elastic strands in the laminate.

In one embodiment, the waistband has a length in the direction parallel to the longitudinal axis of the article of greater than about 12 mm, greater than about 15 mm, greater than about 20 mm. In one embodiment, the waistband has a length in the direction parallel to the longitudinal axis of the article f less than about 50 mm, less than about 45 mm, less than about 40 mm.

In one embodiment, the waistband in a relaxed product has a length in the direction parallel to the lateral axis of the article of greater than about 50 mm, greater than about 75 mm, greater than about 100 mm. In one embodiment, the length in the direction parallel to the lateral axis of the article of the waistband in a relaxed product is less than about 300 mm, less than about 250 mm, less than about 200 mm.

In one embodiment, the CD Length Ratio of the waistband compared to the distance from one tape to the other tape is less than about 2, less than about 1.5, about 1.

In one embodiment, the waistband is on the body-facing surface of the article. In one embodiment, the waistband is on the garment-facing surface of the article. In one embodiment, the waistband is sandwiched in between the layers of the absorbent article. In one embodiment, the waistband is on the garment-facing surface in either the first or second waist regions and on the body-facing surface in either the first or second waist regions. In one embodiment, the waistband is on both the body-facing surface and the garment-facing surface. In one embodiment, the waistband is on either the body-facing surface or the garment-facing surface and the surface not comprising the waistband is printed with a printed waistband feature.

In one embodiment, the distance from one tape edge to the other tape edge is at least about 50% the average length of the baby waist circumference for an average baby that wears the size of absorbent article; at least about 60% the average length; at least about 65% the average length.

In one embodiment, the elastic strands of the waistband laminate may have different installed elongations within one laminate, thus, after being cut, resulting in a first waistband having a first installed elongation and a second waistband having a second installed elongation; both the first and second waistbands have the same applied waistband strain. The installed elongation is the strain at which the elastic is under relative to the second material that it is combined with (e.g. low basis weight nonwoven). For example, if the elastic is stretched from 100 mm to 250 mm when it is combined with the nonwoven, it would be said to be 150% installed elongation or ((250 mm/100 mm)−1)×100%. This laminate can then be allowed to relax and will return to about the original 100 mm, but with 250 mm of nonwoven. There can be more than one installed elongation within one waistband laminate if the elastics are strained to a different degree. For example, strand (1) is stretched from 100 mm to 250 mm when combined with the nonwoven or has 150% installed elongation while strand (2) is stretched from 90 mm to 250 mm when combined with the NW or has an installed elongation of about 178%.

The Applied Waistband Strain is the strain that the waistband laminate is under when combined with the absorbent article. For example if 100 mm of laminate is stretched to 170 mm when applied it would be considered to be 70% applied waistband strain or ((170 mm-100 mm)/100 mm×100%). In one embodiment, the first installed elongation of any number of elastic strands is about 100%, about 125%, about 140%, about 150%, about 160%, about 175%, about 200%. In one embodiment the second installed elongation of any number of elastic strands is about 100%, about 125%, about 140%, about 150%, about 160%, about 175%, about 200%.

In one embodiment, the delta between the first installed elongation and the second installed elongation is greater than about 20%, greater than about 30%, greater than about 40%.

In one embodiment, the resulting Front-to-Back Delta Chassis Contraction is greater than about 5.0%, greater than about 9.0%, greater than about 9.5%, greater than about 12.5%, greater than about 15%, greater than about 20%.

In one embodiment, the Front-to-Back Delta Chassis Contraction is less than about 15%, less than about 12.5%, less than about 10%, less than about 9.5%, less than about 9% when either the front chassis contraction or the back chassis contraction is greater than about 18%, greater than about 20%.

Figure 9A:
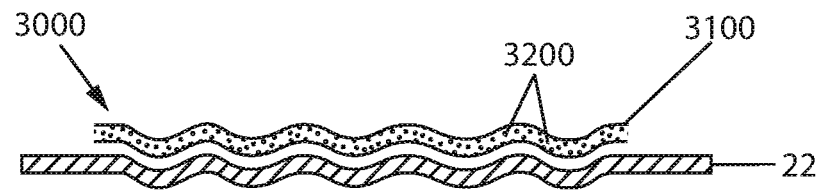
FIGS. 9a-d are schematic cross section views of waistband laminates suitable in embodiments of the invention.
Figure 9B:
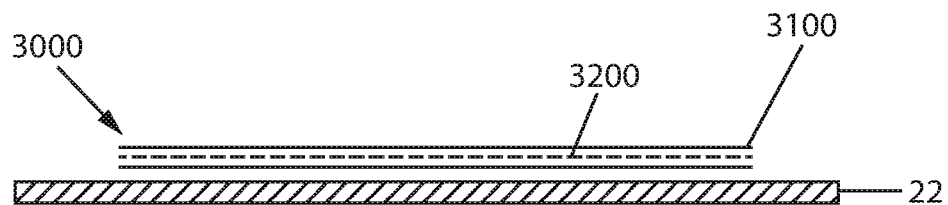
Figure 9C:
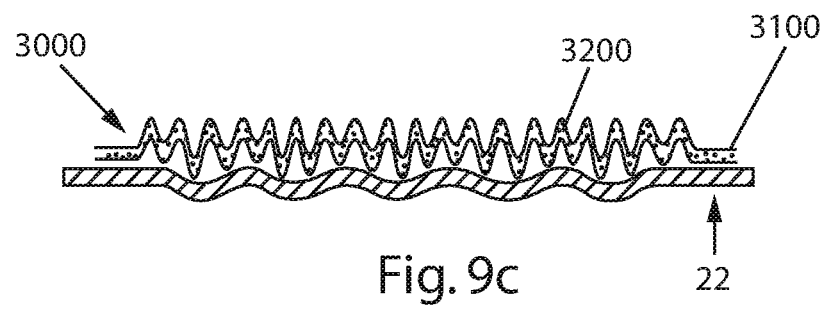
Figure 9D:
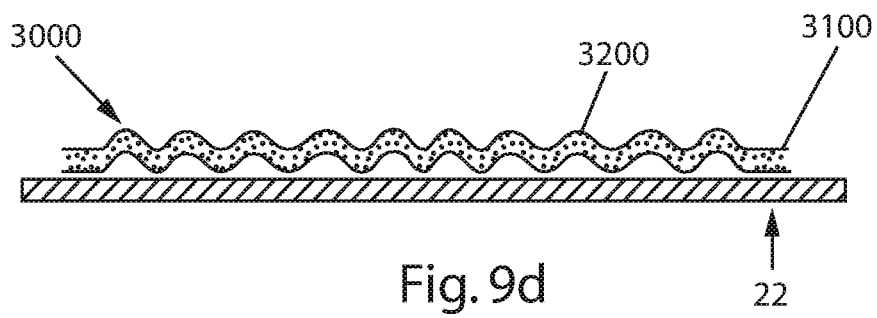

Another object of the present invention is to deliver a better balance of thickness (caliper)/cushion and contraction in a waistband than what is currently known in the art. Presently, most waistbands are either foam based which have good cushion/caliper for comfort and containment but are limited in the amount of contraction or the waistbands are a combination of elastic strands and nonwoven where the elastic strands are pulled at high strain which delivers high contraction, but very little caliper/cushion in use. Thus, one embodiment of the present invention is directed to "consolidation" which provides a waistband having the nonwoven material and the elastic strand(s) combined under a higher first strain (installed elongation) and the resulting waistband attached to the article under a lower applied waistband strain, such that the folded up nonwoven in the waistband provides a cushion/caliper in both the relaxed and stretched/in use states. FIG. 9 depicts cross sectional views of the waistband laminate (3000). FIGS. 9a-b depict cross sections of the waistband with no extended consolidation. FIG. 9a depicts a relaxed product cross section at the waist, parallel to the lateral axis of the diaper chassis (22). FIG. 9b shows an extended product cross section at the waist, parallel to the lateral axis of the diaper. FIGS. 9c-d depict cross sections of the waistband with extended consolidation. FIG. 9c shows a relaxed product cross section at the waist, parallel to the lateral axis of the diaper. FIG. 9c shows that the frequency and amplitude of the waistband is higher than that of the chassis it is applied to. FIG. 9d shows an extended product cross section at the waist, parallel to the lateral axis of the diaper. FIG. 9d shows that even when the chassis is extended, the waistband still has gathers and caliper.

In one embodiment, the waistband is comprised of a laminate comprising a nonwoven material and at least one elastic strand, wherein the nonwoven material and the elastic strand(s) are combined under a first strain and the waistband is attached to the article under an applied waistband strain. In one embodiment, the first strain, also referred to as the installed strand elongation, is greater than about 50%, greater than about 75%, greater than about 100%, greater than about 150%, greater than about 200%, greater than about 225%, greater than about 250%, greater than about 300%, greater than about 350%, greater than about 375%. In one embodiment, the applied waistband strain, also referred to as the waistband strain is greater than about 25%, greater than about 50%, greater than about 75%, greater than about 100%. In one embodiment, the difference between the first strain and the applied waistband strain, also referred to as Consolidation, is greater than about 0%, greater than about 65%, greater than about 75%, greater than about 100%, greater than about 150%, greater than about 200%, greater than about 225%, greater than about 250%, greater than about 300%.

In one embodiment, the waistband has a Full Waistband Consolidation greater than about 95%, greater than about 100%, greater than about 125%, greater than about 150%, greater than about 175%, greater than about 200%.

In one embodiment, the waistband had an Extended Waistband Consolidation greater than about 35%, greater than about 50%, greater than about 75%, greater than about 100%, greater than about 125%, greater than about 175%.

In one embodiment, the waistband is attached near the waist edge. In one embodiment, the waistband is attached within 20 mm of the waist edge. In one embodiment, the waistband is attached flush with the waist edge. In one embodiment, the waistband is present only at one waist edge. In one embodiment, the waistband is present at both the first and second waistband edges.

The nonwoven material and the elastic strand(s) may be combined with adhesive, mechanical bonds, or any other forms of attachment known in the art. The waistband may be attached to the article with adhesive, mechanical bonds, or any other forms of attachment known in the art.

In one embodiment, the relaxed caliper of the waistband is greater than about 1.60 mm, greater than about 2.00 mm, greater than about 2.25 mm, greater than about 2.50 mm.

In one embodiment, the extended caliper of the waistband is greater than about 0.80 mm, greater than about 1.00 mm, greater than about 1.25 mm.

Figure 3:
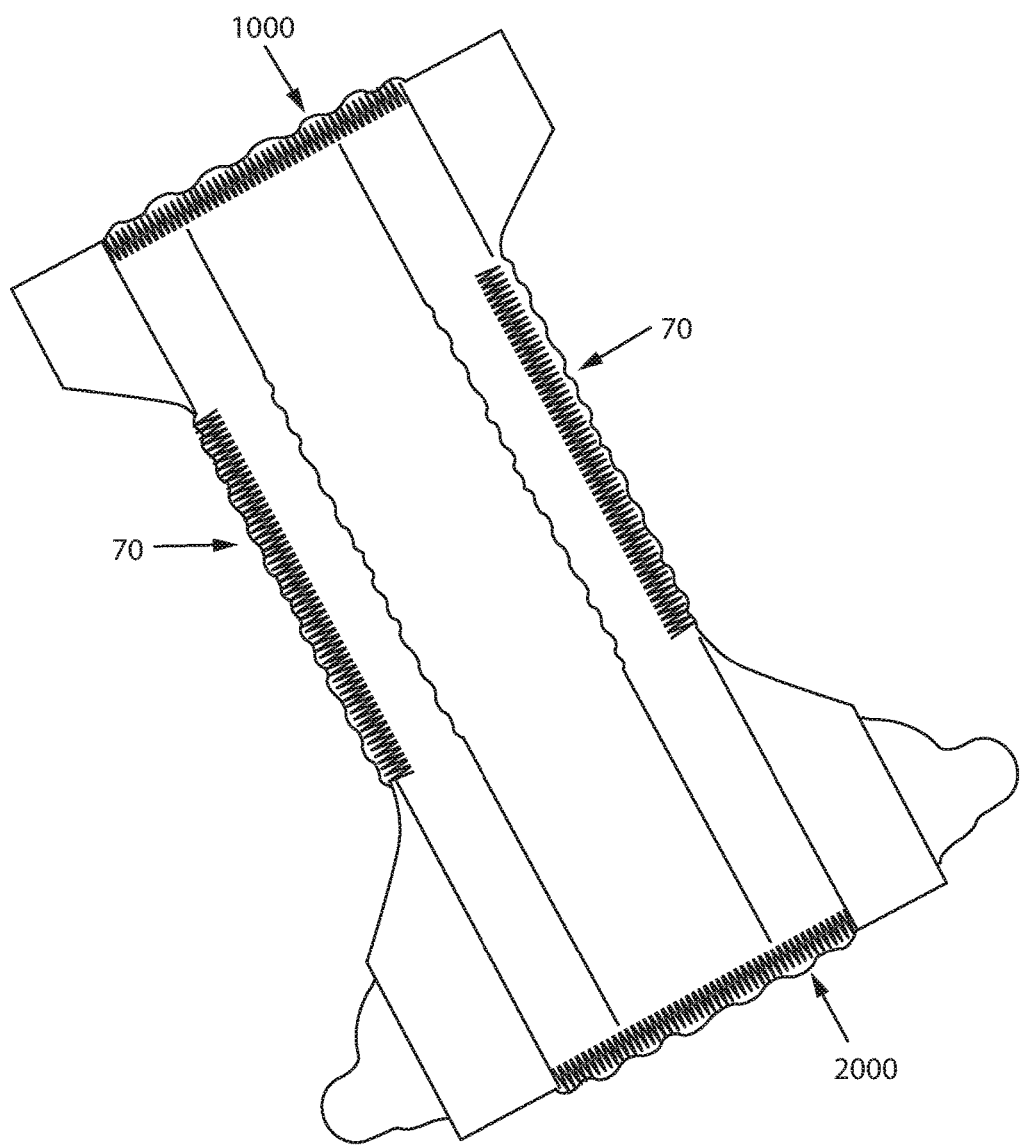
FIG. 3 is a plan view of an absorbent article suitable in one embodiment of the invention.

Another object of the present invention is to deliver an integrated leg gasketing system and front/back waistband feature that provides extra leakage protection around the perimeter of the article. Thus, one embodiment of the present invention is directed to "360 Leakage Protection" which provides a common leg gasketing system and waistband with similar construction having similar gather counts. Additional embodiments may include leg gasketing systems and waistbands that overlap or have similar tints, textures, bond patterns, colors, or other visual cues. FIG. 3 depicts an embodiment having gathers in both the waistband regions and leg gasketing system.

In one embodiment, the disposable absorbent article comprising a waistband and a leg gasketing system, as described herein, wherein the leg gasketing system has a first gather count and the waistband has a second gather count such that the ratio of the first gather count to the second gather count is greater than about 0.5, greater than about 0.75, less than about 1.25, less than about 1.50. In one embodiment, the ratio of the first gather count to the second gather count is about 1.00. In one embodiment, the ratio of the first gather count to the second gather count is from about 0.75 to about 1.25. In one embodiment, the ratio of the first gather count to the second gather count is from about 0.75 to about 1.25, when the leg gasketing system gather count is greater than about 13. In one embodiment, the ratio of the first gather count to the second gather count is from about 0.75 to about 1.25, when the waistband gather count is greater than about 12. In one embodiment, the ratio of the first gather count to the second gather count is from about 0.75 to about 1.25, when the absorbent article is a taped-type product.

In one embodiment, both of the waistband and leg gasketing system comprise elastic strands; in one embodiment, the waistband comprises elastic strands; in one embodiment, both the waistband and leg gasketing system comprise the same type of stretch material and/or laminate structure.

In one embodiment, the waistband has greater than about 10 gathers per 30 mm section, greater than about 12 gathers per 30 mm section. In one embodiment, the leg gasketing system has greater than about 10 gathers per 30 mm section, greater than about 12 gathers per 30 mm section.

In one embodiment, the waistband is present in the first waist edge and the second waist edge and the leg gasketing system is present in the first longitudinal edge and the second longitudinal edge.

Figure 4:
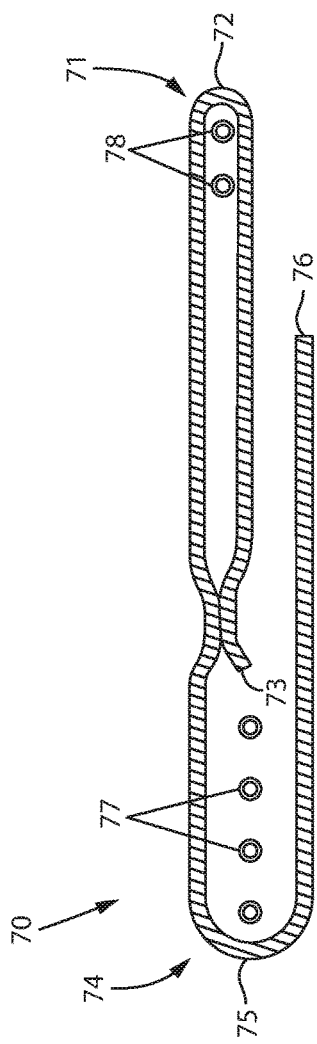
FIG. 4 is a schematic cross section view of an example of a folded outer leg cuff suitable in one embodiment of the invention.
Figure 5:
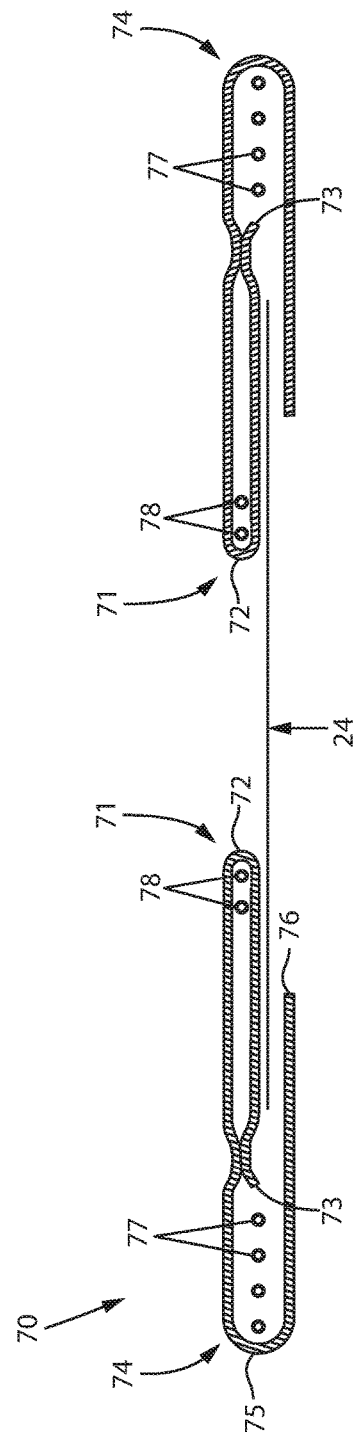
FIG. 5 is a schematic cross section view of an example of a folded outer leg cuff suitable in one embodiment of the invention.

The absorbent article 20 may include a leg gasketing system 70 as described in U.S. Patent Applications 61/480,663 and 61/480,670, both filed on Apr. 29, 2011. FIGS. 4 and 5 depict schematic cross section views of exemplary leg gasketing systems. The leg gasketing system 70 may comprise an inner barrier leg cuff 71 comprising an inner cuff folded edge 72 and an inner cuff material edge 73. The leg gasketing system 70 may further comprise an outer cuff 74 comprising an outer cuff folded edge 75 and an outer cuff material edge 76.

In one embodiment, the leg gasketing system 70 comprises one web of material. An embodiment having one web of material may provide a cost advantage over embodiments having more than one web of material. Further, an embodiment having one web of material may have fewer leaks, as there are no holes created by bonding more than one web of material. Also, an embodiment having one web of material may be more aesthetically pleasing, as few mechanical bonds are visible.

In one embodiment, the leg gasketing system 70 has an inner barrier leg cuff 71 comprised of an inner cuff folded edge 72 and an inner cuff material edge 73. The leg gasketing system 70 may further comprise an outer cuff 74 comprising an outer cuff folded edge 75 and an outer cuff material edge 76. In one embodiment, the web of material is folded laterally inward to form the outer cuff folded edge 75 and folded laterally outward to form the inner cuff folded edge 72. In one embodiment, the leg gasketing system 70 extends from the first waist edge 36 to the second waist edge 38 and is joined to the topsheet 24 and/or backsheet 26 between the inner cuff folded edge 72 and the outer cuff folded edge 75 in the crotch region 37. In one embodiment, the outer cuff material edge 76 is disposed laterally inboard the inner cuff material edge 73.

In one embodiment, the outer leg cuff 74 comprises elastic members 77 positioned in a lateral array between the outer cuff folded edge 75 and outer cuff material edge 76; the outer leg cuff 74 optionally comprises at least two elastic members 77, at least three elastic member 77, at least four elastic members 77, at least five elastic members 77, at least six elastic members 77. In one embodiment, the elastic members 77 may be disposed between the outer cuff folded edge 75 and the inner cuff material edge 73.

In one embodiment, the inner barrier leg cuff 71 comprises an array of elastic members 78 in the area of the inner cuff folded edge 72; the inner barrier leg cuff 71 optionally comprises at least one elastic member 78, at least two elastic members 78, at least three elastic members 78, at least four elastic members 78, at least five elastic members 78. In one embodiment, the elastic members 78 may be disposed between the inner cuff folded edge 72 and the outer cuff material edge 76.

In one embodiment, the leg gasketing system 70 has an inner barrier leg cuff 71 comprised of an inner cuff folded edge 72 and an inner cuff material edge 73. The leg gasketing system 70 may further comprise an outer cuff 74 comprising an outer cuff folded edge 75 and an outer cuff material edge 76. The leg gasketing system may comprise a first material comprising the inner barrier leg cuff 71 and a second material comprising the outer cuff 74. The first and second material may overlap and be joined together along a longitudinal edge of each material by any suitable joining means. In one embodiment, the web of material is folded laterally inward to form the outer cuff folded edge 75 and folded laterally outward to form the inner cuff folded edge 72. In one embodiment, the proximal edges of the outer cuff 74 are coterminous.

One advantage of the leg gasketing system 70 of the present invention is that when a substantially liquid-impervious material is used in construction of the cuff, the polymeric film layer may be narrowed or not present at all, resulting in more cost effective designs. Utilizing adhesive technologies that are more reliably processed results in more reliable performance and creates substantially liquid impervious seals. This technology enables narrowing the film layer to be only slightly wider than the absorbent core by reducing the need for redundant seals.

In one embodiment of the present invention, the backsheet polymeric film is less than about 50 mm wider than the absorbent core; optionally less than about 40 mm wider, less than about 30 mm wider. In one embodiment, the backsheet polymeric film is at lest about 20 mm more narrow than the chassis width; optionally at least about 40 mm more narrow than the chassis width; optionally at least about 60 mm more narrow than the chassis width; optionally at least about 80 mm more narrow than the chassis width; optionally at least about 100 mm more narrow than the chassis width; optionally at least about 120 mm more narrow than the chassis width.

In one embodiment of the present invention, an opacity strengthening patch 80 may be included. The opacity strengthening patch 80 is an additional layer of material. The opacity strengthening patch 80 may be connected to the leg gasketing system 70, the polymeric film layer, or the backsheet 26. The opacity strengthening patch 80 may be disposed between the backsheet 26 and leg gasketing system 70 in either the first waist region 36, the second waist region 38, or both the first waist region 36 and the second waist region 38 of the article; the opacity strengthening patch 80 may overlap at least one of the leg gasketing system 70 or the polymeric film layer. The opacity strengthening patch 80 may be attached to one or both of the leg gasketing system 70 or the polymer film layer using any suitable means such as glue, mechanical bonds, thermal bonds, or the like, so that loads generated during the application process or during wear can be transferred from the lateral edge of the article to the leg gasketing system 70 and/or the polymeric film layer. The opacity strengthening patch is useful in providing the strength needed to prevent the article from extending excessively during application and wearing; it also may provide opacity at the sides and waist to prevent the skin of the user from showing through the article. Thus, the patch 80 may be located at any portion of the chassis where strength and opacity is desirable. Materials suitable to act as the opacity strengthening patch include materials having a basis weight of at least about 10 gsm, at least about 15 gsm, at least about 25 gsm. An opacity strengthening patch useful herein may exhibit the following tensile properties in the cross direction: at 2% engineering strain for a 1 inch wide sample, 0.4N; at 5% engineering strain for a 1 inch wide sample, 1.25N; at 10% engineering strain for a 1 inch wide sample, 2.5N. One opacity strengthening patch useful herein is available from Pegas, Znojmo, CZ, as supplier number 803968.

In one embodiment, the material of the leg gasketing system 70 is made from a substantially liquid impervious material. The material may be selected from the group consisting of an SMS nonwoven, SMMS nonwoven material, or a nonwoven component layer comprising "N-fibers".

Various nonwoven fabric webs may comprise spunbond, meltblown, spunbond ("SMS") webs comprising outer layers of spunbond thermoplastics (e.g., polyolefins) and an interior layer of meltblown thermoplastics. In one embodiment of the present invention, the leg gasketing cuff 70 comprises a nonwoven component layer having fine fibers ("N-fibers") with an average diameter of less than 1 micron (an "N-fiber layer") may be added to, or otherwise incorporated with, other nonwoven component layers to form a nonwoven web of material. In some embodiments, the N-fiber layer may be used to produce a SNS nonwoven web or SMNS nonwoven web, for example. N-fibers are further discussed in WO 2005/095700 and U.S. patent application Ser. No. 13/024,844.

Figure 6:
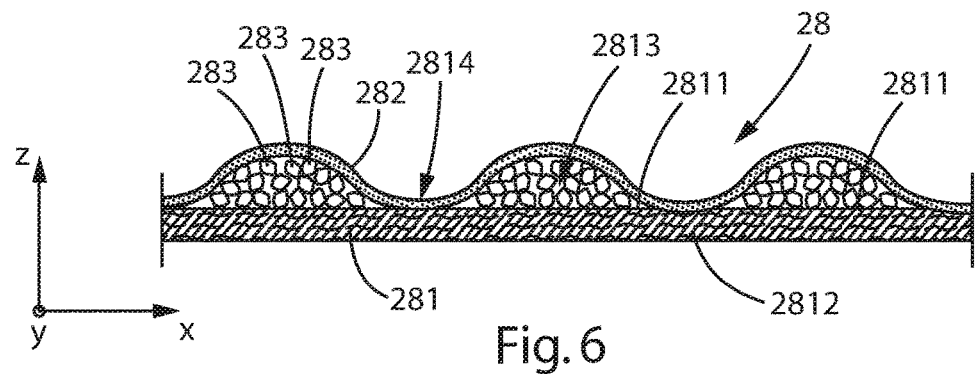
FIG. 6 is a schematic cross section view of an example of an absorbent core suitable in one embodiment of the invention.
Figure 7:
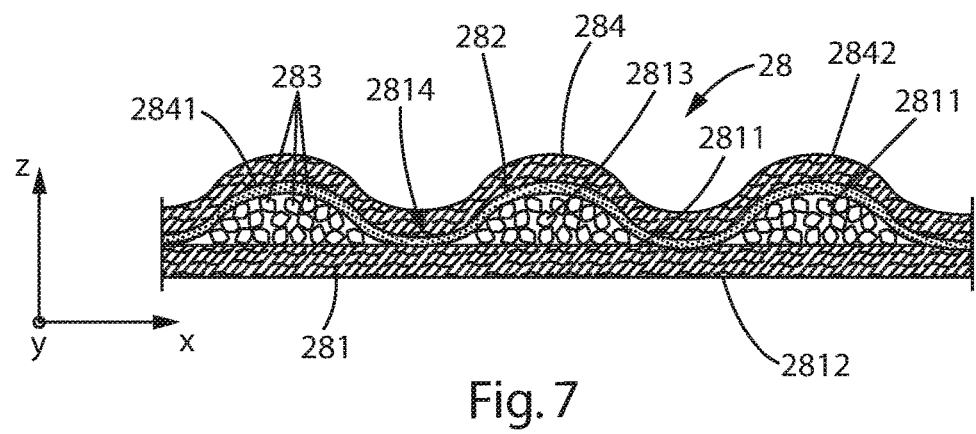
FIG. 7 is a schematic cross section view of another example of an absorbent core suitable in one embodiment of the invention.
Figure 8:
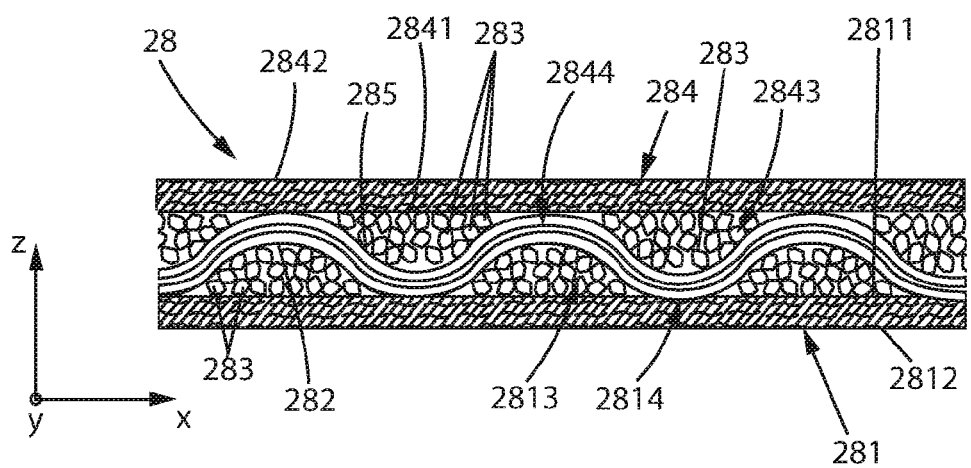
FIG. 8 is a schematic cross section view of another example of an absorbent core suitable in one embodiment of the invention.

In one embodiment, an absorbent article includes an absorbent core 28 that is substantially cellulose free, as described in U.S. Pat. No. 7,750,203; U.S. Pat. No. 7,744,576, and U.S. Patent Publication No. 2008/0312617A1. Cross-sectional views of examples of suitable absorbent cores are schematically represented in FIGS. 6-8. In one embodiment, an absorbent core 28 comprises first and second layers of material 281, 282 and an absorbent material 283 disposed between the first and second layers 281, 282. In one embodiment the first and second layers of material can be a fibrous material chosen from at least one of a nonwoven fibrous web, a woven fibrous web and a layer of thermoplastic adhesive material. Although the first and second layers can be made of a same material, in one embodiment, the first layer 281 is a nonwoven fibrous web and the second layer 282 is a layer of thermoplastic adhesive material. A nonwoven fibrous web 281 can include synthetic fibers, such as mono-constituent fibers of PE, PET and PP, multi-constituent fibers such as side by side, core/sheath or island in the sea type fibers. Such synthetic fibers may be formed via a spunbonding process or a meltblowing process. The nonwoven fibrous web 281 may include a single layer of fibers but it may also be advantageous to provide the nonwoven web with multiple layers of fibers such as multiple layers of spunbond fibers, multiple layers of meltblown fibers or combinations of individual layer(s) of spunbond and meltblown fibers. In one embodiment, the nonwoven web 281 can be treated with an agent (such as a surfactant) to increase the surface energy of the fibers of the web. Such an agent renders the nonwoven web more permeable to liquids such as urine. In another embodiment, the nonwoven web can be treated with an agent (such as a silicone) that lowers the surface energy of the fibers of the nonwoven web. Such an agent renders the nonwoven web less permeable to liquids such as urine.

The first layer 281 comprises a first surface 2811 and a second surface 2812 and at least regions 2813 of the first surface are in direct facial relationship with a significant amount of absorbent material 283. In one embodiment an absorbent material is deposited on the first surface 2811 in a pattern to form regions 2813 on the first layer 281, which are in direct facial relationship with a significant amount of absorbent polymer material 283 and regions 2814 on the first web that are in facial relationship with only an insignificant amount of absorbent material. By "direct facial relationship with a significant amount of absorbent material" it is meant that some absorbent material is deposited on top of the regions 2813 at a basis weight of at least 100 g/m$^2$, at least 250 g/m$^2$ or even at least 500 g/m$^2$. The pattern may include regions that all have the same shape and dimensions (i.e. projected surface area and/or height). In the alternative the pattern may include regions that have different shape or dimensions to form a gradient of regions.

In one embodiment, the second layer 282 is a layer of a thermoplastic adhesive material. "Thermoplastic adhesive material" as used herein is understood to mean a polymer composition from which fibers are formed and applied to the absorbent material with the intent to immobilize the absorbent material in both the dry and wet state. Non-limiting examples of thermoplastic adhesive material may comprise a single thermoplastic polymer or a blend of thermoplastic polymers. The thermoplastic adhesive material may also be a hot melt adhesive comprising at least one thermoplastic polymer in combination with other thermoplastic diluents such as tackifying resins, plasticizers and additives such as antioxidants. In certain embodiments, the thermoplastic polymer has typically a molecular weight (Mw) of more than 10,000 and a glass transition temperature (Tg) usually below room temperature or $-6°$ C.$>$Tg$<16°$ C. In certain embodiments, typical concentrations of the polymer in a hot melt are in the range of about 20 to about 40% by weight. Exemplary polymers are (styrenic) block copolymers including A-B-A triblock structures, A-B diblock structures and (A-B)n radial block copolymer structures wherein the A blocks are non-elastomeric polymer blocks, typically comprising polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof. Other suitable thermoplastic polymers that may be employed are metallocene polyolefins, which are polymers prepared using single-site or metallocene catalysts. In exemplary embodiments, the tackifying resin has typically a Mw below 5,000 and a Tg usually above room temperature, typical concentrations of the resin in a hot melt are in the range of about 30 to about 60% by weight, and the plasticizer has a low Mw of typically less than 1,000 and a Tg below room temperature, with a typical concentration of about 0 to about 15%.

The thermoplastic adhesive material 282 can be disposed substantially uniformly within the absorbent material 283. In the alternative, the thermoplastic adhesive material 282 can be provided as a fibrous layer disposed on top of the absorbent material 283 and the regions 2814 of the first surface 2811 that are in facial relationship with only an insignificant amount of absorbent material. In one embodiment, a thermoplastic adhesive material is applied at an amount of between 1 and 20 g/m², between 1 and 15 g/m² or even between 2 and 8 g/m². The discontinuous deposition of absorbent material on the first layer 281 imparts an essentially three-dimensional structure to the fibrous layer of thermoplastic material 282. In other words, the layer of thermoplastic adhesive material follows the topography resulting from the absorbent material 283 deposited on the first nonwoven fibrous web 281 and the regions 2814 that only include insignificant amounts of absorbent material. Without intending to be bound by any theory, it is believed that the thermoplastic adhesive materials disclosed herein enhance immobilization of the absorbent material in a dry and wet state.

In one embodiment, the absorbent core 28 may further comprise a second layer of a nonwoven fibrous material 284. This second layer may be provided of the same material as the nonwoven fibrous layer 281, or in the alternative may be provided from a different material. It may be advantageous for the first and second nonwoven fibrous layers 281, 284 to be different in order to provide these layers with different functionalities.

The regions 2813 may have any suitable shape in the x-y dimension of the absorbent core. In one embodiment, the regions 2813 form a pattern of disc that are spread on the first surface of the first web 281. In one embodiment, the regions 2813 form a pattern of longitudinal "strips" that extend continuously along the longitudinal axis of the absorbent core (i.e. along the y dimension). In an alternative embodiment, these strips may be are arranged to form an angle of at between 10 and 90 degrees, between 20 and 80 degrees, between 30 and 60 degrees, or even 45 degrees relative to the longitudinal axis of the absorbent article.

In one embodiment, the second nonwoven layer 284 has a first surface 2841 and a second surface 2842 and an absorbent material 283 applied to its first surface 2841 in order to form a pattern of regions 2843 that are in direct facial relationship with a significant amount of absorbent material 283 and regions 2844 on the first surface 2841 that are in facial relationship with only an insignificant amount of absorbent material as previously discussed. In one embodiment, a thermoplastic adhesive material 285 may further be applied on top of the second nonwoven layer 284 as previously discussed in the context of the first web/absorbent material/thermoplastic adhesive material composite. The second nonwoven layer 284 may then be applied on top of the first nonwoven layer 281. In one embodiment, the pattern of absorbent material present on the second nonwoven layer 284 may be the same as the pattern of absorbent material present on the first nonwoven layer 281. In an other embodiment, the patterns of absorbent material that are present on the first and second nonwoven layers are different in terms of at least one of the shape of the regions, the projected surface areas of the regions, the amount of absorbent material present on the regions and the type of absorbent material present on the regions.

The absorbent core 28 may also comprise an auxiliary adhesive which is not illustrated in the figures. The auxiliary adhesive may be deposited on at least one of or even both the first and second nonwoven layers 281, 284 before application of the absorbent material 283 in order to enhance adhesion of the absorbent material as well as adhesion of the thermoplastic adhesive material 282, 285 to the respective nonwoven layers 281, 284. The auxiliary adhesive may also aid in immobilizing the absorbent material and may comprise the same thermoplastic adhesive material as described hereinabove or may also comprise other adhesives including but not limited to sprayable hot melt adhesives, such as H. B. Fuller Co. (St. Paul, Minn.) Product No. HL-1620-B. The auxiliary adhesive may be applied to the nonwoven layers 281, 284 by any suitable means, but according to certain embodiments, may be applied in about 0.5 to about 1 mm wide slots spaced about 0.5 to about 2 mm apart. Non-limiting examples of suitable absorbent material 283 include absorbent polymer material such as cross linked polymeric materials that can absorb at least 5 times their weight of an aqueous 0.9% saline solution as measured using the Centrifuge Retention Capacity test (Edana 441.2-01). In one embodiment, the absorbent material 283 is absorbent polymer material which is in particulate form so as to be flowable in the dry state.

EXAMPLES

Differential Contraction

| Products | Front Waist Relaxed Chassis Width (mm) RCFW | Front Stretched Chassis Width (mm) ECFW | Front Chassis Contraction (%) FCC | Back Waist Relaxed Chassis Width (mm) RCBW | Back Stretched Chassis Width (mm) ECBW | Back Chassis Contraction (%) BCC | Front-to-Back Delta in Chassis Contraction (%) Delta CC |
|---|---|---|---|---|---|---|---|
| Anerle Diaper (1) | 294 | 330 | 10.91 | 296 | 332 | 10.84 | 0.1 |
| Parents Choice Diaper (2) | 251 | 286 | 12.24 | 247 | 288 | 14.24 | 2.0 |

| Products | Front Waist Relaxed Chassis Width (mm) RCFW | Front Stretched Chassis Width (mm) ECFW | Front Chassis Contraction (%) FCC | Back Waist Relaxed Chassis Width (mm) RCBW | Back Stretched Chassis Width (mm) ECBW | Back Chassis Contraction (%) BCC | Front-to-Back Delta in Chassis Contraction (%) Delta CC |
|---|---|---|---|---|---|---|---|
| Moony Diaper (3) | 202 | 232 | 12.93 | 197 | 238 | 17.23 | 4.3 |
| Huggies Baby Steps (4) | 296 | 340 | 12.94 | 299 | 335 | 10.75 | 2.2 |
| Huggies Supreme (5) | 251 | 270 | 6.91 | 231 | 270 | 14.34 | 7.4 |
| Drypers (6) | 300 | 350 | 14.29 | 284 | 332 | 14.46 | 0.2 |

(1) Anerle Taped Diaper from Philippines, Size L (9-13 kg), SKU 90324495220, Lot 20121009 WP071157C9236; green foam sandwiched waistband
(2) Parents Choice Taped Diaper (2) from North America, Lot 9344 M02 1759 S-1855; white foam sandwiched waistband
(3) Moony Taped Diaper from Japan, Lot 910193071; green foam sandwiched waistband
(4) Huggies Baby Steps US, 1991, Size 4, Lot 3U251910248; white foam sandwiched waistband in blue film
(5) Huggies Supreme 2001, Size 4, Lot NM127501F0755; green nonwoven waistband with small denier elastic strands in white film
(6) Drypers, US, Size Large, Sep. 8, 1998; white foam sandwiched waistband white film

| Examples | Front Waist Relaxed Chassis Width (mm) RCFW | Front Stretched Chassis Width (mm) ECFW | Front Chassis Contraction (%) FCC | Back Waist Relaxed Chassis Width (mm) RCBW | Back Stretched Chassis Width (mm) ECBW | Back Chassis Contraction (%) BCC | Front-to-Back Delta Chassis Contraction (%) Delta CC |
|---|---|---|---|---|---|---|---|
| A | 171 | 212.2 | 24.1 | 160 | 212.4 | 32.8 | 8.7 |
| B | 175.2 | 212.6 | 21.3 | 165.2 | 212.6 | 28.7 | 7.3 |
| C | 179.6 | 212.6 | 18.4 | 166.2 | 212.6 | 27.9 | 9.5 |
| D | 179.4 | 212.4 | 18.4 | 164.2 | 212.8 | 29.6 | 11.2 |
| E | 191.2 | 212.4 | 11.1 | 163.6 | 212.4 | 29.8 | 18.7 |
| F | 184.6 | 212.2 | 15.0 | 170.6 | 212.6 | 24.6 | 9.7 |
| G | 199.4 | 212.2 | 6.4 | 163.6 | 212.6 | 30.0 | 23.5 |
| H | 192.4 | 212.6 | 10.5 | 165 | 213 | 29.1 | 18.6 |
| I | 201.6 | 212.4 | 5.4 | 165 | 212.4 | 28.7 | 23.4 |
| J | 208.8 | 212.8 | 1.9 | 164.2 | 212.8 | 29.6 | 27.7 |

A - Installed Elongation: 150%; Waistband Strain: 150%; Delta Front/Back Installed Elongation: 0
B - Installed Elongation: 200%; Waistband Strain: 200%; Delta Front/Back Installed Elongation: 0
C - Installed Elongation: 150%; Waistband Strain: 130%; Delta Front/Back Installed Elongation: 20
D - Installed Elongation: 200%; Waistband Strain: 180%; Delta Front/Back Installed Elongation: 20
E - Installed Elongation: 150%; Waistband Strain: 110%; Delta Front/Back Installed Elongation: 40
F - Installed Elongation: 200%; Waistband Strain: 160%; Delta Front/Back Installed Elongation: 40
G - Installed Elongation: 150%; Waistband Strain: 100%; Delta Front/Back Installed Elongation: 50
H - Installed Elongation: 200%; Waistband Strain: 140%; Delta Front/Back Installed Elongation: 60
I - Installed Elongation: 200%; Waistband Strain: 120%; Delta Front/Back Installed Elongation: 80
J - Installed Elongation: 200%; Waistband Strain: 100%; Delta Front/Back Installed Elongation: 100

Consolidation

| Products | Relaxed Caliper (mm) | Extended Caliper (mm) | Extended Length CEL (mm) | Relaxed Length RWL (mm) | Total Length EWL (mm) | Full Waistband Consolidation (%) | Extended Waistband Consolidation (%) |
|---|---|---|---|---|---|---|---|
| Huggies Snug & Dry (7) | 0.91 | 0.55 | 237 | 172 | 273 | 59 | −14 |
| Huggies Little Movers (8) | 1.08 | 0.61 | 223 | 155 | 241 | 56 | −14 |
| Huggies Overnight (9) | 1.45 | 0.70 | 220 | 131 | 253 | 93 | 33 |
| K | 1.64 | 0.40 | 205 | 125 | 201 | 60 | −1 |
| L | 2.24 | 0.71 | 208 | 132 | 286 | 116 | 53 |
| M | 2.40 | 1.04 | 203 | 130 | 340 | 162 | 98 |

-continued

| Products | Relaxed Caliper (mm) | Extended Caliper (mm) | Extended Length CEL (mm) | Relaxed Length RWL (mm) | Total Length EWL (mm) | Full Waistband Consolidation (%) | Extended Waistband Consolidation (%) |
|---|---|---|---|---|---|---|---|
| N | 2.54 | 1.01 | 205 | 131 | 386 | 195 | 131 |
| O | 2.22 | 1.29 | 205 | 126 | 425 | 237 | 176 |

(7) Huggies Snug & Dry, size 4; Lot No. BI 103108B
(8) Huggies Little Movers, size 3; Lot No. BI 024610B
(9) Huggies Overnight, size 4; Lot No. PA 027104F
K - 75% Installed Elongation and 75% Waistband Strain
L - 150% Installed Elongation and 75% Waistband Strain
M - 225% Installed Elongation and 75% Waistband Strain
N - 300% Installed Elongation and 75% Waistband Strain
O - 375% Installed Elongation and 75% Waistband Strain 360 Leakage Protection

| Products | Average Leg Gasketing System Gather Count | Average Waistband Gather Count | Ratio of Leg Gasketing System Gather Count to Waistband Gather Count |
|---|---|---|---|
| P | 20.7 | 22.2 | 0.9 |
| Q | 21.2 | 21.2 | 1.0 |
| R | 16.7 | 18.2 | 0.9 |
| Huggies Baby Steps (4) | 23.2 | 12.5 | 1.9 |
| Huggies Supreme (5) | 17.0 | 24.0 | 0.7 |
| Anerle Diaper (1) | 20.0 | 16.0 | 1.3 |
| Parent Choice (2) | 20.0 | 15.5 | 1.3 |
| Moony Diaper (3) | 12.5 | 11.2 | 1.1 |

P - 150% Installed Elongation, 75% Waistband Strain
R - 150% Installed Elongation, 75% Waistband Strain
Q - 150% Installed Elongation, 75% Waistband Strain Test Methods Chassis Contraction Method The chassis contraction is measured using a calibrated ruler capable of measuring to ±1 mm, (traceable to National standards such as NIST), and a force gauge capable of measuring an applied force of 500 g accurately to ±0.5 g (a suitable gauge is the Chatillon DFS series, available from Ametek, Largo, Fla.). A spring loaded clamp, with contact faces 60 mm wide by 10 mm deep, is attached to the force gauge to hold the test article. All testing is performed in a room maintained at about 23±2° C. and about 50±2% relative humidity. All samples were conditioned for 2 hours before testing at about 23±2° C. and about 50±2% relative humidity.

For this measure the chassis is identified as the portion of the article with contiguous back sheet and does not include any attached tabs or attached elastic tabs/ears. Unfold the absorbent article taking care not to stretch the waist features. Place it on a horizontal bench surface with the back sheet facing the bench and the top sheet facing upward. If present, unfold and lie flat any tabs or ears attached to the back half of the article. Identify the back waist feature of the article. With the article flat against the bench, lay the calibrated ruler along the article aligning it with the lateral midline of the waist feature. Measure the lateral distance from the right distal edge of the chassis to the left distal edge of the chassis and record to the nearest 1 mm. This is the Relaxed Back Chassis Width (RBCW)

Attach the force gauge to the right distal edge of the chassis. As attached, the force gauge is oriented to pull from left to right. The grip faces are parallel to the longitudinal axis of the article, centered at the lateral midline of the waist feature, with 3 mm of the chassis within the grip faces.

Adhere a piece of 2-sided adhesive tape 50 mm in width by 900 mm long to the bench. Hold the article with the back sheet directed toward the taped surface with the back waist parallel to the long dimension of the tape. Align the lateral midline of the waist feature with the lateral midline of the tape strip. Secure the first 3 mm of the left chassis edge to the adhesive tape. Using the force gauge, extend the back waist to an applied force of 500 g. Next lower the article and adhere the article's back waist to the adhesive tape across the lateral width of the chassis. Remove the force gauge from the chassis. Lay the ruler across the article aligning it along the lateral midline of the waist feature. Measure the lateral distance from the right distal edge of the chassis to the left distal edge of the chassis and record to the nearest 1 mm. This is the Extended Back Chassis Width (EBCW).

Repeat this measure in like fashion for the front waist feature of the article to determine the Relaxed Front Chassis Width (RFCW) and the Extended Front Chassis Width (EFCW). Calculate the Chassis Contractions as follows:

% Back Chassis Contraction (% BCC)=(EBCW−RBCW)/EBCW×100

% Front Chassis Contraction (% FCC)=(EFCW−RFCW)/EFCW×100

Front-to-Back Delta Chassis Contraction=absolute value of (% BCC−% FCC)

Waist Feature Calipers

Calipers were performed using an Ono Sokki digital caliper (GS-503 Linear Gauge Sensor with DG-3610 Digital Gauge, Ono Sokki Co, Japan) capable of measuring to 0.01 mm. The foot diameter is 1 cm and the applied pressure is 0.5 psi. Readings are taken after a residence time of 5 sec. Linear measurements are made using a calibrated ruler capable of measuring to ±1 mm (traceable to National standards such as NIST). A stainless steel plate, uniformly 1.5 mm thick ±0.1 mm, 20 cm wide and 40 cm long is used for mounting the extended waist. All testing is performed in a room maintained at about 23±2° C. and about 50±2% relative humidity. All samples are conditioned for 2 hours before testing at about 23±2° C. and about 50±2% relative humidity.

Relaxed Waist Calipers

Unfold an absorbent article taking care not to stretch the waist features. Place it on a horizontal bench surface with the back sheet facing the bench and the top sheet facing upward. If present, unfold and lie flat any tabs or ears attached to the back half of the article. Identify the back waist feature of the article. Using a calibrated ruler measure the lateral width of the waist feature along its longitudinal midline. This is the Relaxed Length of the waist feature (RWL) Mark the waist feature along its midline at 50% of its lateral width. This is waist site 1 (WS1). Measure and mark two more sites, the first 1.5 cm to the left of the 50% mark (WS2) and the second 1.5 cm to the right of the 50% mark (WS3).

Place the caliper on the anvil and zero the digital controller. Place the article on the anvil, with the top sheet facing upward, and use the caliper to measure the thickness at WS1, WS2, and WS3. Report to the nearest 0.01 mm as the Relaxed Waist Caliper RWC1, RWC2, and RWC3 respectively.

Using a cryogenic freeze spray (available as CytoFreeze, Control Company, TX) gently remove the elastic feature from the article. Place the article on the anvil, with the top sheet facing upward, and use the caliper to measure the thickness of the article corresponding to WS1, WS2, and WS3. Report to the nearest 0.01 mm as Relaxed Back Sheet Caliper RBC1, RBC2, RBC3 respectively.

Calculate the Waist Feature Caliper as:

Relaxed Waist Feature Caliper=[(RWC1−RBC1)+ (RWC2−RBC2)+(RWC3−RBC3)]/3

Repeat this procedure for three identical articles and report as the average to the nearest 0.01 mm.

Extended Waist Calipers

Unfold an absorbent article taking care not to stretch the waist features. Assemble a vertical ring stand which supports a horizontal bar. Attach a spring loaded clamp to the left edge of the chassis, centered on the waist feature. Attach the clamp to the horizontal support so that the waist feature hangs vertically. Attach a second clamp, which has a mass of 300 g±1 g, to the right edge of the chassis, centered on the midline of the waist feature. Allow the article to hang for 30 seconds and then using the calibrated ruler measure the extended length of the waist feature to the nearest 1 mm. This is the Chassis Extended Length (CEL). The CEL can be used for all extended waist measures.

Unfold another absorbent article taking care not to stretch the waist features. Place it on a horizontal bench surface with the back sheet facing the bench and the top sheet facing upward. If present, unfold and lie flat any tabs or ears attached to the back half of the article. Identify the back waist feature of the article. Using a calibrated ruler measure the lateral width of the waist feature along its longitudinal midline. This is the Relaxed Length of the waist feature (RWL) Mark the waist feature along its midline at 50% of its lateral width. This is waist site 1 (WS1). Measure and mark two more sites, the first 1.5 cm to the left of the 50% mark (WS2) and the second 1.5 cm to the right of the 50% mark (WS3). Identify the proximal edge of the waist feature, i.e. the edge closest to the crotch of the article. Mark a lateral line 1.5 cm from the proximal edge toward the crotch, and parallel to the waist feature. Along a longitudinal axis that passes through WS1, mark the intersection at the lateral line just drawn (AS1). Repeat in like fashion for WS2 and WS3 to define sites AS2 and AS3 respectively.

Place the article, top sheet facing upward, onto the stainless steel plate. Secure the left distal edge of the chassis at the waist feature's midline to the steel plate with adhesive tape. Grasp the right side of the chassis and pull until the waist feature has been extended equal to the Chassis Extended Length (CEL). Secure the right side of the chassis to the steel plate with adhesive tape.

Place the steel plate with attached article on the anvil of the caliper. Place the caliper foot on a region of the steel plate that is not covered by the article and zero the digital control. Using the caliper, measure the thickness at the six marked sites. Report to the nearest 0.01 mm as Extended Waist Caliper EWC1, EWC2, and EWC3. Using a cryogenic freeze spray gently remove the elastic feature from the article. Place the steel plate with attached article on the anvil of the caliper and measure the thickness of the article at the sites corresponding to WS1, WS2 and WS3. Report to the nearest 0.01 mm as Extended Back Sheet Caliper EBC1, EBC2, EBC3 respectively.

Calculate the Waist Feature Calipers as:

Extended Waist Feature Caliper=[(EWC1−EBC1)+ (EWC2−EBC2)+(EWC3−EBC3)]/3

Repeat this procedure for three identical articles and report as the average to the nearest 0.01 mm.

Waist Feature Percent Consolidation

Linear measurements are made using a calibrated ruler capable of measuring to ±1 mm (traceable to National standards such as NIST). All testing is performed in a room maintained at about 23±2° C. and about 50±2% relative humidity. All samples are conditioned for 2 hours before testing at about 23±2° C. and about 50±2% relative humidity.

Unfold the absorbent article taking care not to stretch the waist features. Place it on a horizontal bench surface with the back sheet facing the bench and the top sheet facing upward. If present, unfold and lie flat any tabs or ears attached to the back half of the article. Identify the back waist feature of the article. Using a calibrated ruler measure the lateral width of the waist feature along its midline and record to the nearest 1 mm. This is the Relaxed Length of the waist feature (RWL).

Using a cryogenic freeze spray (available as CytoFreeze, Control Company, TX) carefully remove the waist feature from the article. Place the waist feature into a beaker with 100 mL of dichloromethane and soak for 15 minutes to dissolve the adhesives. Remove the waist feature from the solvent and remove the elastics. Lay the waist feature substrate flat in a fume hood to dry. Assemble a vertical ring stand which supports a horizontal bar. Attach a spring loaded clamp, which is at least as wide as the waist feature, to the left edge of the waist feature. Attach the clamp to the horizontal support so that the waist feature hangs vertically. Attach a second clamp, which has a mass of 3 g±1 g and is at least as wide as the waist feature, to the right edge of the waist feature. Allow the article to hang for 30 seconds and then using the calibrated ruler measure the extended length of the waist feature to the nearest 1 mm. This is the Extended Waist Feature Length (EWL). Calculate the Full Waistband Consolidation as:

% Full Waistband Consolidation=(EWL−RWL)/ RWL×100

Repeat this procedure for three identical articles and report as the average to the nearest 1 mm.

Calculate the Extended Waistband Consolidation as:

% Extended Waistband Consolidation=(EWL−RWL)/ RWL×100−(1−((CEL−RWL)/CEL)*100)

Repeat this procedure for three identical articles and report as the average to the nearest 1 mm.

Frequency of Waistband and Outer Leg Cuff Gathers on Taped Diaper Products

In the visual center of the waistband on the diaper both CD and MD, report the number of gathers per 30 mm on both taped end (TE) and un-taped end (UTE). Hold in place the measuring template, as shown in FIG. 10, then count the gather peaks within the 30 mm window on the template. Make sure not to stretch the gathers. Perform this on both the taped (TE) inside and outside and then repeat on the un-taped end (UTE) inside and outside of the product. Report the number of gathers within the 30 mm.

In the visual center of the Leg Gasketing System gather on the diaper both CD and MD, report the number of gathers per 30 mm on both Baby right and Baby left. Hold in place the measuring template then count the number of gathers within the 30 mm window on the template. Make sure not to stretch the gathers. Perform this on both Baby right and Baby left of the product both CD and MD. Report the number of gathers within the 30 mm.

Calculate the Ratio of Leg Gasketing System Gather Count to Waistband Gather Count as follows:

Ratio=Average Leg Gasketing System Gather Count/ Average Waistband Gather Count

Repeat this procedure for three identical articles and report as the average.

CD Length Ratio

CD Length Ratio is the ratio of chassis extended length (CEL) to Extended Back Chassis Width (EBCW), as defined here.

Calculate the CD Length Ratio as follows:

CD Length Ratio=CEL/EBCW

Repeat this procedure for three identical articles and report as the average.

The dimensions and values disclosed herein are not to be understood as being strictly limited to the exact numeral values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article comprising: a first waist region, a second waist region, a crotch region disposed between the first waist region and second waist region; a first waist edge and a second waist edge; the disposable absorbent article comprising a first waistband near the first waist edge and a second waistband near the second waist edge, wherein the first waistband has a Relaxed Front Chassis Width and an Extended Front Chassis Width; wherein the second waistband has a Relaxed Back Chassis Width and an Extended Back Chassis Width; wherein the first waistband has a % Front Chassis Contraction, wherein % Front Chassis Contraction=((Extended Front Chassis Width−Relaxed Front Chassis Width)/Extended Front Chassis Width)×100; wherein the second waistband has a % Back Chassis Contraction, wherein % Back Chassis Contraction=((Extended Back Chassis Width−Relaxed Back Chassis Width)/Extended Back Chassis Width)×100; wherein the disposable absorbent article has a Front-to-Back Delta Chassis Contraction of greater than 5.0% and less than 27.7%, wherein the Front-to-Back Delta Chassis Contraction=absolute value of (% Back Chassis Contraction−% Front Chassis Contraction); wherein the second waistband has an Extended Waist Feature Length and a Chassis Extended Length, wherein the second waistband has a ratio of Extended Waist Feature Length to Chassis Extended Length of greater than 1.16 and less than 2.07; and wherein the disposable absorbent article is a taped diaper.

2. The disposable absorbent article of claim 1, wherein both the first waistband and the second waistband are comprised of a waistband laminate.

3. The disposable absorbent article of claim 2, wherein the waistband laminate is comprised of a nonwoven material and at least two elastic strands, wherein each of the at least two elastic strands have different installed elongations.

4. The disposable absorbent article of claim 3, wherein the waistband laminate is cut between the at least two elastic strands to generate the first waistband and the second waistband, wherein the first waistband is comprised of the nonwoven material and at least one elastic strand and the second waistband is comprised of the nonwoven material and at least one elastic strand.

5. The disposable absorbent article of claim 4, wherein both the first waistband and the second waistband are applied to the disposable absorbent article and the first waistband has a first installed elongation and the second waistband has a second installed elongation.

6. The disposable absorbent article of claim 5, wherein the first installed elongation is about 100% and the second installed elongation is about 150%.

7. The diposable absorbent article of claim 5, wherein the first installed elongation is about 140% and the second installed elongation is about 160%.

8. The disposable absorbent article of claim 5, wherein the delta between the first installed elongation and the second installed elongation is greater than 20% and less than or equal to 100%.

9. The disposable absorbent article of claim 2, wherein the waistband laminate is comprised of a nonwoven material and at least two elastic strands, wherein each of the at least two elastic strands are different elastic materials.

10. The disposable absorbent article of claim 2, wherein the waistband laminate is comprised of a nonwoven material and at least one elastic strand, wherein where the waistband laminate is cut results in Chassis Contraction, measured as defined herein, only on one side of the waistband laminate.

11. The disposable absorbent article of claim 2, wherein the first waistband and the second waistband are applied to the disposable absorbent article at an applied waistband strain of from about 70% to about 75%.

12. The disposable absorbent article of claim 2, wherein the waistband laminate is comprised of a nonwoven material and at least eight elastic strands, wherein four of the elastic strands have a first installed elongation and the other four of the elastic strands have a second installed elongation.

13. The disposable absorbent article of claim 12, wherein the waistband laminate is cut between the at least eight elastic strands to generate the first waistband and the second waistband, wherein the first waistband is comprised of the nonwoven material and four elastic strands and the second waistband is comprised of the nonwoven material and four elastic strands.

14. The disposable absorbent article of claim 1, wherein both the first waistband and the second waistband are comprised of a waistband laminate, wherein the waistband laminate is cut such that the two resulting waistbands have an unequal distribution of elastic strands.

15. A disposable absorbent article comprising: a first waist region, a second waist region, a crotch region disposed between the first waist region and second waist region; a first waist edge and a second waist edge; the disposable absorbent article comprising a first waistband near the first waist edge and a second waistband near the second waist edge, wherein the first waistband has a Relaxed Front Chassis Width and an Extended Front Chassis Width; wherein the second waistband has a Relaxed Back Chassis Width and an Extended Back Chassis Width; wherein the first waistband has a % Front Chassis Contraction, wherein % Front Chassis Contraction=((Extended Front Chassis Width−Relaxed Front Chassis Width)/Extended Front Chassis Width)×100; wherein the second waistband has a % Back Chassis Contraction, wherein % Back Chassis Contraction=((Extended Back Chassis Width)/Relaxed Back Chassis Width)/Extended Back Chassis Width)×100; wherein the absorbent article has a Front-to-Back Delta Chassis Contraction of less than 12.5% and either a % Front Chassis Contraction, or a % Back Chassis Contraction, that is greater than 18%; wherein the Front-to-Back Delta Chassis Contraction=absolute value of (% Back Chassis Contraction−% Front Chassis Contraction); wherein the second waistband has an Extended Waist Feature Length and a Chassis Extended Length, wherein the waistband has a ratio of Extended Waist Feature Length to Chassis Extended Length of greater than 1.16 and less than 2.07; and wherein the disposable absorbent article is a taped diaper.

16. The disposable absorbent article of claim 15, wherein both the first waistband and the second waistband are comprised of a waistband laminate.

17. The disposable absorbent article of claim 16, wherein the waistband laminate is comprised of a nonwoven material and at least two elastic strands, wherein the at least two elastic strands have different installed elongations.

18. The disposable absorbent article of claim 17, wherein the waistband laminate is cut between the at least two elastic strands to generate the first waistband and the second waistband, wherein the first waistband is comprised of the nonwoven material and at least one elastic strand and the second waistband is comprised of the nonwoven material and at least one elastic strand.

19. The disposable absorbent article of claim 18, wherein both the first waistband and the second waistband are applied to the disposable absorbent article and the first waistband has a first installed elongation and the second waistband has a second installed elongation.

20. The disposable absorbent article of claim 16, wherein the waistband laminate is comprised of a nonwoven material and at least two elastic strands, wherein each of the at least two elastic strands are different elastic materials.

\* \* \* \* \*